(12) United States Patent
Alvarez et al.

(10) Patent No.: US 7,329,666 B2
(45) Date of Patent: Feb. 12, 2008

(54) DERIVATIVES OF VARIOLIN B

(75) Inventors: Mercedes Alvarez, Barcelona (ES); José Luis Fernández Puentes, Leon (ES); David Ferández Bleda, Barcelona (ES)

(73) Assignee: Pharma Mar, S.A., Madrid (ES)

( * ) Notice: Subject to any disclaimer, the term of this patent is extended or adjusted under 35 U.S.C. 154(b) by 0 days.

(21) Appl. No.: 10/343,391

(22) PCT Filed: Aug. 3, 2001

(86) PCT No.: PCT/GB01/03517

§ 371 (c)(1),
(2), (4) Date: Aug. 29, 2003

(87) PCT Pub. No.: WO02/12240

PCT Pub. Date: Feb. 14, 2002

(65) Prior Publication Data
US 2004/0058939 A1 Mar. 25, 2004

(30) Foreign Application Priority Data
Aug. 3, 2000 (GB) .............................. 0019117.1

(51) Int. Cl.
C07D 471/14 (2006.01)
A61K 31/505 (2006.01)
(52) U.S. Cl. ........................ 514/267; 544/250
(58) Field of Classification Search ................ 544/250; 514/267
See application file for complete search history.

(56) References Cited

U.S. PATENT DOCUMENTS

2005/0014778 A1   1/2005 Morris et al. ............... 514/292

FOREIGN PATENT DOCUMENTS

WO   WO 02/04447    1/2002
WO   WO 03/006457   1/2003

OTHER PUBLICATIONS

Anderson et al., Studies toward the total synthesis of the variolins: rapid entry to the core structure, Tetrahedron Letters 42(2), pp. 311-313, Jan. 2001.*
Alvarez et al., Synthesis of deoxyvariolin B, Tetrahedron Letters, 42(2), pp. 315-317, Jan. 2001.*
Perry et al., Alkaloids from the Antarctic sponge *Kirkpatrikia variolosa*, Tetrahedron, vol. 50, No. 13, pp. 3987-3994, 1994.*
Simone, Oncology: Introduction, Cecil Textbook of Medicine, 20th Edition, vol. 1, pp. 1004-1010, 1996.*
Alvarez, M. et al., "Synthesis of deoxyvariolin B", *Tetrahedron Letters*, 42(2), pp. 315-317 (2001).
Alvarez, Mercedes et al., "Synthesis of 1, 2-dihydropyrrolo[1,2-c]primidin-1-ones", *J. Chem. Soc. Perkins Trans. I*, pp. 249-255 (1999).
Alvarez, Mercedes et al., "Synthesis of 3-Aryl- and 3-Heteroaryl-7-azaindoles", *Synthesis*, pp. 615-620 (1999).
Anderson,R.J. et al., "Studies toward the total synthesis of the variolins: rapid entry to the core structure", *Tetrahedron Lett.*, vol. 42(2), pp. 311-313 (2001).
Capuano, Lilly et al., "Heterocyclizations, XIII) New Polycyclic Pyrimidines with Bridge-Head Nitrogen", *Chem. Ber.*, 107, pp. 929-936 (1974).
Desarbre, Eric et al., "Synthesis of 2-Substituted-1H-Pyrrolo[2,3-b] Pyridines: Preparation of 7-Azaolivacine Analogue and 7-Azaindolopyridopyrimidine Derivatives", *Tetrahedron*, 53(10), pp. 3637-3648 (1997).
Erba et al., "Cell cycle phase perturbation and apoptosis induced by Variolin B, a novel antitumor agent of marine origin", *Proc. Am. Assoc. Can. Res. Annual Meeting*, vol. 27, #198 pp. 28-29 (1996).
Fresneda, Pilar M. et al., "Synthetic studies towards the 2-aminopyrimidine alkaloids variolins and meridianins from marine origin", *Tetrahedron Lett.*, 41(24), pp. 4777-4780 (2000).
Girgis, Nabih S. et al., "The Synthesis of 5-Azaindoles by Substitution-Rearrangement of 7-Azaindoles upon Treatment with Certain Primary Amines", *J. Heterocyclic Chem.*, vol. 26, No. 2, pp. 317-325 (1989).
Katritzky, Alan R. et al., *Comprehensive Hetercyclic Chemistry*, Pergamon Press, Oxford, vol. 3, p. 111 (1984).
Katritzky, Alan R. et al., "Activation of the 2-Alkyl Group of a 2-Alkylindole toward Proton Loss and Subsequent Electrophilic Substitution", *J. Am. Chem. Soc.*, vol. 108, No. 21, pp. 6808-6809 (1986).
Lorenz et al. "A New Indole Synthesis", *J. Org. Chem.*, vol. 30, pp. 2531-2533 (1965).
Majeed, Amera J. et al., "Stannylation Reactions and Cross-Couplings in Pyrimidines", *Tetrahedron*, vol. 45, No. 4, pp. 993-1006 (1989).
Mendiola, Javier et al., "Reaction of 2-Bromomethylazoles and TosMIC: A Domino Process to Azolopyrimidines. Synthesis of Core Tricycle of the Variolins Alkaloids", *Organic Letters*, vol. 2, No. 21, 3253-3256 (2000).
Perry,Nigel B. et al., "Alkaloids from the Antarctic sponge *Kirkpatrickia varialosa*. Part 1: Variolin B, a new antitumor and antiviral compound" *Tetrahedron*, 50(13), pp. 3987-3992 (1994).
Sawayama, Tadahiro et al., "Displacement Reactions of 2-Alkysulfonyl-4-Chloropyrimidine Derivatives with Nucleophiles", *Heterocycles*, vol. 8, pp. 299-305 (1977).

(Continued)

Primary Examiner—Deepak Rao
(74) Attorney, Agent, or Firm—Fish & Richardson P.C.

(57) ABSTRACT

The invention provides antitumour compounds of formula (I), wherein $R^1$ is an aromatic substituent; $R^2$ is hydrogen or a substituent when the dotted line is absent, or $R^2$ is absent when the dotted line represents a bond to give a double bond between the nitrogen which bears $R^2$ and the carbon which bears $R^3$; $R^3$ is an oxo group =O when the dotted line is absent or is a substituent when the dotted line represents a bond to give a double bond between the nitrogen bearing $R^2$ and the carbon bearing $R^3$; $R^4$ is hydrogen or a substituent; and pharmaceutically acceptable salts thereof.

23 Claims, No Drawings

OTHER PUBLICATIONS

Perry, Nigel B. et al., "Alkaloids from the Antarctic Sponge *Kirkpatrickia varialosa*. Part 2: Variolin A and N(3')-methyl tetrahydrovariolin B", *Tetrahedron*, vol. 50, No. 13, pp. 3993-4000 (1994).

Vorbrüggen et al., Syntheses of Nucleosides—Amination of Hetercycles—A New Simple Synthesis of Cytidines, *Liebigs Annalen Der Chemie*, pp. 988-1002 (1975).

Calabresi et al. "Chemotherapy of Neoplastic Diseases", Goodman & Gilman's The Pharmacological Basis of Therapeutics, 9th ed. New York: McGraw-Hill, 1996, pp. 1225-1229.

Charya et al. "Wynthesis and Evaluation of Sulphonylhydrazones of Phthalimido Acetaldehyde as Anticancer Agents." J. Indian Chem Soc. vol. 75, Jan. 1998, pp. 46-48.

* cited by examiner

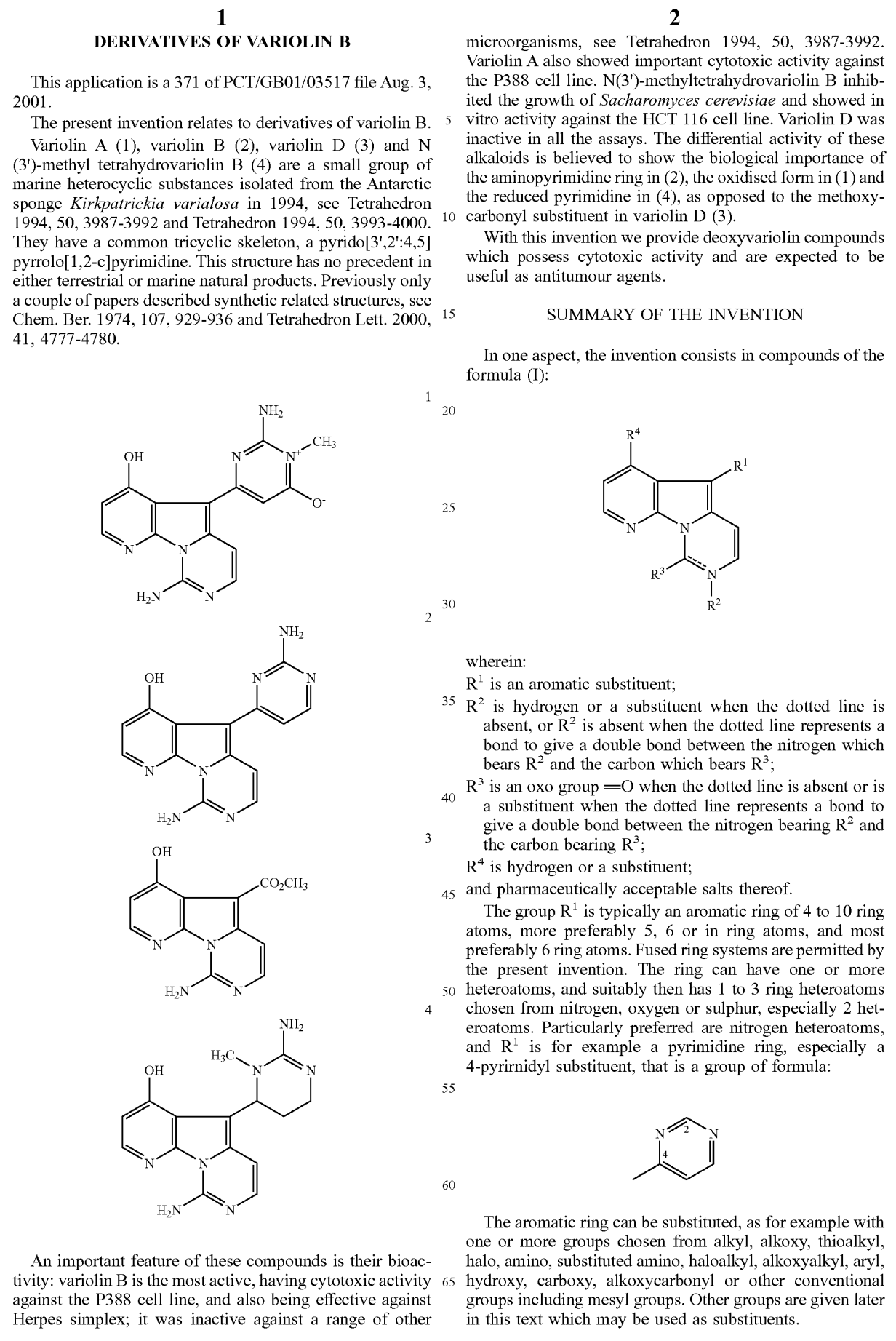

DERIVATIVES OF VARIOLIN B

This application is a 371 of PCT/GB01/03517 file Aug. 3, 2001.

The present invention relates to derivatives of variolin B.

Variolin A (1), variolin B (2), variolin D (3) and N (3')-methyl tetrahydrovariolin B (4) are a small group of marine heterocyclic substances isolated from the Antarctic s $R^2$ when present is preferably hydrogen, a nitrogen protecting group, or some other substituent. Examples of nitrogen protecting groups such as methoxymethyl or tosyl are well known and do not need to be given in detail. Examples of other substituents include any group which can be substituted at this position by reaction of the compound where $R^1$ is hydrogen. More generally, reference is made to the other groups given later in this text.

$R^3$ is an oxo group or can be a substituent such as might be introduced by reaction of the oxo compound, including amino, substituted amino including protected amino, thioalkyl. More generally, reference is made to the other groups given later in this text.

$R^4$ is hydrogen or a substituent such as alkoxy especially methoxy, hydroxy, halo especially chloro, or other group which might be introduced by nucleophilic substitution or by other derivatisation, including thioalkyl or mesyl. When $R^4$ is hydrogen, the compounds are deoxyvariolin B derivatives. When $R^4$ is hydroxy, the compounds are variolin B derivatives. More generally, reference is made to the other groups given later in this text.

$R^1$ is preferably a 4-pyrimidyl group substituted at the 2-position. Suitable substituents include an amino group and derivatives thereof such as N-acyl, especially N-acetyl. Other nucleophilic substituents are envisaged, such as alkoxy or alkylthio substituents, especially a methylthio group.

$R^2$ is preferably absent.

$R^3$ is preferably an amino group and derivatives thereof such as N-acyl, especially N-acetyl.

$R^4$ is preferably hydrogen.

The dotted line preferably represents a bond.

A particularly preferred class of compounds includes those compounds of the formula (I) wherein:

$R^1$ is a 4-pyrimidyl group substituted at the 2-position with amino, N-acyl especially N-acetyl, alkylthio especially a methylthio group, alkyl- or aryl-sulphinyl especially methanesulphinyl, or alkyl- or aryl-sulphonyl especially methanesulphonyl;

$R^2$ is absent;

$R^3$ is an optionally protected amino group or N-acyl, especially N-acetyl; and $R^4$ is hydrogen, hydroxy or methoxy.

The invention also extends to pharmaceutically acceptable salts.

Examples of substituents which may be employed in the present invention include OH, OR', SH, SR', SOR', $SO_2R'$, $NH_2$, NHR', $N(R')_2$, NHCOR', $N(COR')_2$, $NHSO_2R'$, C(=O)R', $CO_2H$, $CO_2R'$, $C_1$-$C_{12}$ alkyl and $C_1$-$C_{12}$ haloalkyl, the or each group R' being independently selected from the group consisting of OH, $C_1$-$C_{12}$ alky, $C_1$-$C_{12}$ haloalkyl, aryl (which may optionally be substituted with a group selected from $C_1$-$C_6$ alkyl, $C_1$-$C_6$ alkoxy, $C_1$-$C_6$ alkylthio, $NH_2$, $C_1$-$C_6$ alkylamino, di($C_1$-$C_6$ alkyl)amino, $NO_2$, CN and halogen), aralkyl or arylalkenyl (the aryl moiety of which may optionally be substituted with a group selected from $C_1$-$C_6$ alkyl $C_1$-$C_6$ alkoxy, $C_1$-$C_6$ alkylthio, $NH_2$, $C_1$-$C_6$ alkylamino, di($C_1$-$C_6$ alkyl)amino, $NO_2$, CN and halogen), and wherein the group $R_1$ is a group of formula $N(R')_2$ or $N(COR')_2$, each of the R' groups may be the same or different, or the two R' groups, together with the nitrogen atom to which they are attached, form a 5-12 membered heterocyclic ring.

In the definitions used in the present specification, alkyl groups may be straight or branched chain groups and preferably have from 1 to about 12 carbon atoms, more preferably 1 to about 8 carbon atoms, still more preferably 1 to about 6 carbon atoms, and most preferably 1, 2, 3 or 4 carbon atoms. Methyl, ethyl and propyl including isopropyl are particularly preferred alkyl groups in the compounds of the present invention. As used herein, the term alkyl, unless otherwise modified, refers to both cyclic and noncyclic groups, although cyclic groups will comprise at least three carbon ring members.

Haloalkyl groups are alkyl groups (including cycloalkyl groups) as defined above which are substituted with one or more halogen atoms (preferably fluorine, chlorine, bromine or iodine) and preferably have from 1 to about 12 carbon atoms, more preferably 1 to about 8 carbon atoms, still more preferably 1 to about 6 carbon atoms, and most preferably 1, 2, 3 or 4 carbon atoms. Methyl, ethyl and propyl including isopropyl groups which are substituted with 1, 2 or 3 halogen atoms which may be the same or different, especially fluoromethyl, fluorochloromethyl, trifluoromethyl and trichloromethyl, are particularly preferred haloalkyl groups in the compounds of the present invention.

Preferred alkenyl and alkynyl groups in the compounds of the present invention have one or more unsaturated linkages and from 2 to about 12 carbon atoms, more preferably 2 to about 8 carbon atoms, still more preferably 2 to about 6 carbon atoms, even more prefereably 2, 3 or 4 carbon atoms. The terms alkenyl and alkynyl as used herein refer to both cyclic and noncyclic groups, although straight or branched noncyclic groups are generally more preferred.

Preferred alkoxy groups in the compounds of the present invention include groups having one or more (but preferably only one) oxygen linkages and from 1 to about 12 carbon atoms, more preferably from 1 to about 8 carbon atoms, and still more preferably 1 to about 6 carbon atoms, and most preferably 1, 2, 3 or 4 carbon atoms.

Preferred alkylthio groups in the compounds of the present invention have one or more (but preferably only one) thioether linkages and from 1 to about 12 carbon atoms, more preferably from 1 to about 8 carbon atoms, and still more preferably 1 to about 6 carbon atoms. Alkylthio groups having 1, 2, 3 or 4 carbon atoms are particularly preferred.

Preferred alkylsulfinyl groups in the compounds of the present invention include those groups having one or more sulfoxide (SO) groups and from 1 to about 12 carbon atoms, more preferably from 1 to about 8 carbon atoms, and still more preferably 1 to about 6 carbon atoms. Alkylsulfinyl groups having 1, 2, 3 or 4 carbon atoms are particularly preferred.

Preferred alkylsulfonyl groups in the compounds of the present invention include those groups having one or more sulfonyl (SO2) groups and from 1 to about 12 carbon atoms, more preferably from 1 to about 8 carbon atoms, and still more preferably 1 to about 6 carbon atoms. Alkylsulfonyl groups having 1, 2, 3 or 4 carbon atoms are particularly preferred.

Preferred alkanoyl groups in the compounds of the present invention include those groups having one or more carbonyl (CO) groups and from 1 to about 12 carbon atoms, more preferably from 1 to about 8 carbon atoms, and still more preferably 1 to about 6 carbon atoms (including the carbonyl carbon). Alkanoyl groups having 1, 2, 3 or 4 carbon atoms, especially the formyl, acetyl, propionyl, butyryl and isobutyryl groups, are particularly preferred.

Preferred alkylamino groups in the compounds of the present invention have one or more (but preferably only one) NH linkages and from 1 to about 12 carbon atoms, more preferably from 1 to about 8 carbon atoms, and still more preferably 1 to about 6 carbon atoms. Alkylamino groups having 1, 2, 3 or 4 carbon atoms, especially the methylamino, ethylamino, propylamino and butylamino groups, are particularly preferred.

Preferred dialkylamino groups in the compounds of the present invention have one or more (but preferably only one) nitrogen atom bonded to two alkyl groups, each of which may from 1 to about 12 carbon atoms, more preferably from 1 to about 8 carbon atoms, and still more preferably 1 to about 6 carbon atoms. The alkyl groups may be the same or different. Dialkylamino groups wherein each alkyl group has 1, 2, 3 or 4 carbon atoms, especially the dimethylamino, diethylamino, N-methylethylamino, N-ethylpropylamino, dipropylamino, dibutylamino and N-methylbutylamino groups, are particularly preferred.

Preferred alkanoylamino groups in the compounds of the present invention have one NH—CO-linkage bonded to an alkyl group having from 1 to about 12 carbon atoms, more preferably from 1 to about 8 carbon atoms, and still more preferably 1 to about 6 carbon atoms. Alkanoylamino groups having 1, 2, 3 or 4 carbon atoms, especially the formylamino, acetylamino, propionylamino and butyrylamino groups, are particularly preferred. The acetylamino group is especially preferred.

Preferred dialkanoylamino groups in the compounds of the present invention have one nitrogen atom bonded to two alkanoyl groups as defined above, each of which may be the same or different and has from 1 to about 12 carbon atoms, more preferably from 1 to about 8 carbon atoms, and still more preferably 1 to about 6 carbon atoms. Dialkanoylamino groups wherein each alkanoyl group has 1, 2, 3 or 4 carbon atoms, especially the diformylamino, formylacetylamino, diacetylamino, dipropionylamino and dibutyrylamino groups, are particularly preferred. The diacetylamino group is especially preferred.

Preferred alkylsulfonylamino groups in the compounds of the present invention have one NH—SO2-linkage bonded to an alkyl group having from 1 to about 12 carbon atoms, more preferably from 1 to about 8 carbon atoms, and still more preferably 1 to about 6 carbon atoms. Alkylsulfonylamino groups having 1, 2, 3 or 4 carbon atoms, especially the methanesulfonylamino, ethanesulfonylamino, propanesulfoylamino and butanesulfonylamino groups, are particularly preferred.

Examples of particular compounds of this invention include the compounds (1), (2), (5), (16), (18) and (21) in the following pages, as well the compound we now designate (20a) which in Scheme 4 is intermediate between compound (20) and (21), where $R^2$ is absent, $R^3$ is acetamido, $R^4$ is hydrogen and $R^1$ is 2-methylthiopyrimidin-4-yl, being a compound of formula:

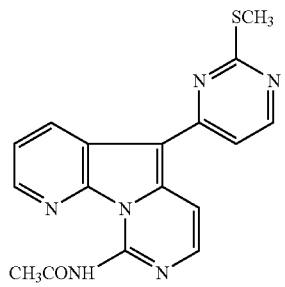

The present invention further provides pharmaceutical compositions comprising a compound of this invention with a pharmaceutically acceptable carrier, and the use of the compounds of this invention in the preparation of a medicament. Methods of treatment are also provided.

Examples of pharmaceutical compositions include any solid (tablets, pills, capsules, granules, etc.) or liquid (solutions, suspensions or emulsions) with suitable composition or oral, topical or parenteral administration, and they may contain the pure compound or in combination with any carrier or other pharmacologically active compounds. These compositions may need to be sterile when administered parenterally.

Administration of the compounds or compositions of the present invention may be by any suitable method, such as intravenous infusion, oral preparations, intraperitoneal and intravenous administration. We prefer that infusion times of up to 24 hours are used, more preferably 2-12 hours, with 2-6 hours most preferred. Short infusion times which allow treatment to be carried out without an overnight stay in hospital are especially desirable. However, infusion may be 12 to 24 hours or even longer if required. Infusion may be carried out at suitable intervals of say 2 to 4 weeks. Pharmaceutical compositions containing compounds of the invention may be delivered by liposome or nanosphere encapsulation, in sustained release formulations or by other standard delivery means.

The correct dosage of the compounds will vary according to the particular formulation, the mode of application, and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The present invention further provides pharmaceutical formulations for combination therapy, comprising a compound of this invention and at least one other therapeutically active compound. The other compound can have antitumour activty, or can can have some other activity of use in conjunction with the antitumour activity of the compounds of this invention.

The other drugs may form part of the same composition, or be provided as a separate composition for administration at the same time or a different time. The identity of the other drug is not particularly limited, and suitable candidates include:

a) drugs with antimitotic effects, especially those which target cytoskeletal elements, including microtubule modulators such as taxane drugs (such as taxol, paclitaxel, taxotere, docetaxel), podophylotoxins or vinca alkaloids (vincristine, vinblastine);

b) antimetabolite drugs such as 5-fluorouracil, cytarabine, gemcitabine, purine analogues such as pentostatin, methotrexate);

c) alkylating agents such as nitrogen mustards (such as cyclophosphamide or ifosphamide);

d) drugs which target DNA such as the antracycline drugs adriamycin, doxorubicin, pharmorubicin or epirubicin;

e) drugs which target topoisomerases such as etoposide;

f) hormones and hormone agonists or antagonists such as estrogens, antiestrogens (tamoxifen and related compounds) and androgens, flutamide, leuprorelin, goserelin, cyprotrone or octreotide;

g) drugs which target signal transduction in tumour cells including antibody derivatives such as herceptin;

h) alkylating drugs such as platinum drugs (cis-platin, carbonplatin, oxaliplatin, paraplatin) or nitrosoureas;

i) drugs potentially affecting metastasis of tumours such as matrix metalloproteinase inhibitors;

j) gene therapy and antisense agents;

k) antibody therapeutics;

l) other bioactive compounds of marine origin, notably the didemnins such as aplidine or the ecteinascidins such as Et 743;

m) anti-emetic drugs, in particular dexamethasone.

The cytotoxicity of the compounds of scheme 4 of this invention is illustrated by the following IC50 μM data:

| compound | P-388 | A-549 | HT-29 |
|---|---|---|---|
| 5 | 0.36 | 0.04 | 0.04 |
| 21 | >3 | 0.16 | 0.16 |
| 20a | >3 | 0.29 | 0.29 |
| vanriolin B | 0.85 | 0.17 | 0.09 |

The invention also extends to a synthesis of the compounds, starting from a 7-azaindole or at a later stage. Preparation of the tricyclic pyridopyrrolopyrimidones (11) was achieved starting from a 7-azaindole by lithiation at carbon 2, introduction of a $C_2$-side chain, then cyclization. A heteroaryl coupling reaction was used for the introduction of the fourth aromatic ring.

Thus, according to the present invention, there is provided a method for preparing the compounds of this invention which involves reaction of an optionally substituted 5-halopyrido[3',2':4,5]pyrrolo[1,2-c]pyrimidine or 8,9-dihydro-5-halopyrido[3',2':4,5]-pyrrolo[1,2-c]pyrimid-9-one with a derivatised aromatic compound such as a stannylaryl compound, notably a trimethylstannylaryl compound, especially a trimethylstannylpyrimidine derivative. The resultant product can be further reacted to change substituent groups. Amino or other reactive substituents in the starting compound can be protected and thereafter deprotected.

Preferred intermedaite compounds of this invention are thus of formula:

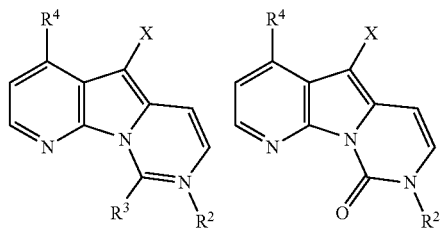

X is halo and $R^2$, $R^3$ and $R^4$ are as defined, particularly wherein X is iodo, $R^2$ is a protecting group, $R^3$ is a protected amino group, and $R^4$ is hydrogen, hydroxy or methoxy.

Our synthetic approach to variolin B has been developed using deoxyvariolin B (5) as a target. We show our retrosynthesis which is based on the preparation of the common pyridopyrrolopyrimidine tricyclic system from a 7-azaindole. The key step is a heteroaryl coupling catalysed by Pd(0) for the introduction of the pyrimidine substituent.

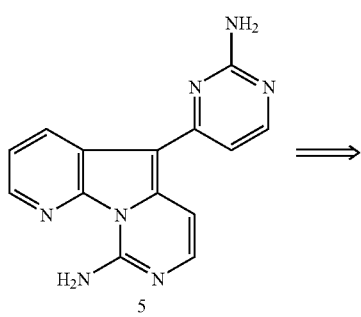

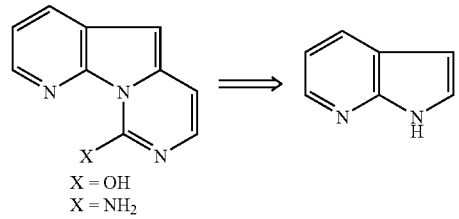

The introduction of a functionalised two-carbon chain at the 2-position of 7-azaindole, see J. Org. Chem. 1965, 30, 2531-2533, was achieved by reaction of a 2-lithio-derivative with 2-phthalimidoacetaldehyde (6), itself obtained in 75% yield from 2-aminoacetaldehyde dimethylacetal by protection of the amino group by reaction with phthalic anhydride in $CH_2Cl_2$ at 140° C. for 15 minutes followed by hydolysis of the acetal group with 10% HCl at reflux. Lithiation of a 7-azaindole had previously been described only for its N-phenylsulphonyl derivative, see Tetrahedron, 1997, 53, 3637-3648. We used the method described by Katritzky, see J. Am. Chem. Soc. 1986, 108, 6808-6809, involving 2-lithiation of the 1-carboxylic acid lithium salt, formed in situ, because we found the yield to be superior to that using the 1-phenylsulphonyl-7-azaindole and additionally, the two separate steps of introduction and removal of the N-protecting group are avoided. Thus, reaction of the bislithio-derivative (7) with aldehyde (6) afforded the alcohol (8) in 44% yield. Protection of the alcohol as a tetrahydropyranyl ether gave a diastereomeric mixture which was not separated because both stereogenic centers are lost later in the synthesis. Hydrazinolysis of the phthalmide residue yielded the amine (9) quantitatively, and this was converted into tetrahydropyrimidone (10) in 76% yield on treatment with triphosgene in $CH_2Cl_2$ with diisopropyl ethylamine (DIPEA) as base. The dihydro-pyrimidone (11) was obtained after removing the hydroxy-protecting group by acid hydrolysis followed by dehydration of the alcohol via the mesylate (Scheme 1).

Scheme 1: Synthesis of pyrido[3',2':4,5]pyrrololl,2-c]pyrimidin-1-one(11)[9]

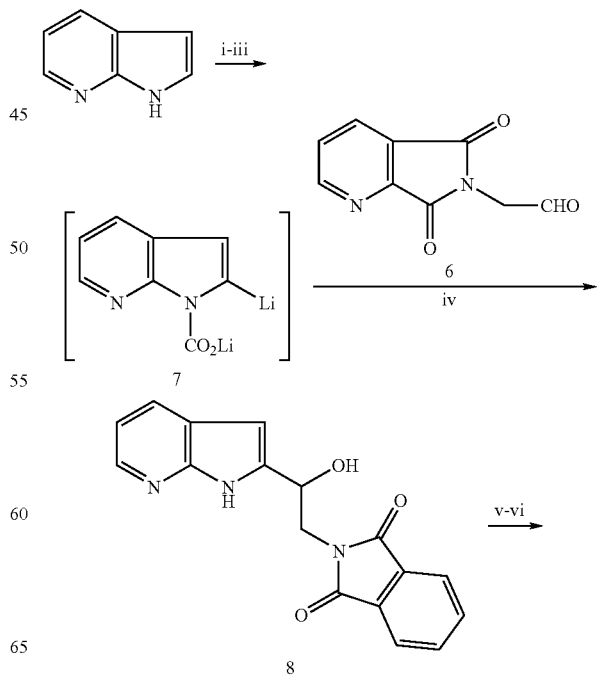

-continued

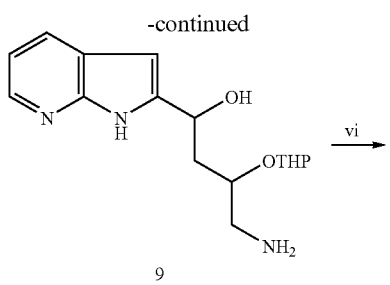

9

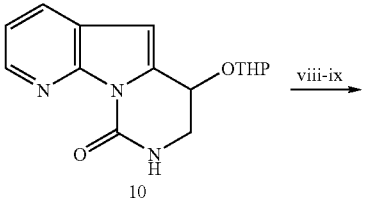

10

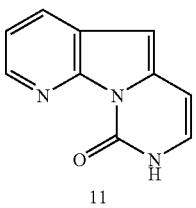

11 i: n-BuLi, THF, −78° C. to rt;
ii: CO₂, −78° C.;
iii: t-BuLi, THF, −78° C.;
iv: 5 THF, −78° C. to rt (44%);
v: DHP, HCl-benzene, CHCl₃, (87%);
vi: NH₂NH₂.H₂O, EtOH, (100%);
vii: (Cl₃CO)₂CO, DIPEA, CH₂Cl₂, rt (76%);
viii:4N HCl, CH₂Cl₂ (100%);
ix: MsCl, TEA, CH₂Cl₂, 0° C. (95%)

With our previous experience in the heteroaryl coupling with 7-azaindole, see Synthesis 1999, 615-620, and in the lithiation of dihydropyrrolo[1,2-c]pyrimidin-1-ones, see J. Soc. Chem. Perkin Trans. L 1999, 249-255, we planned the preparation of the tin derivative (14) from the protected halo-derivative (13). Protection of the tricyclic pyrimidone (11) was achieved with methyl chloromethyl ether using sodium hydride as base in DMF giving (12). Halogenation of (12) using N-bromosuccinimide (NBS) or iodine in potassium hydroxide afforded (13a) (80%) and (13b) (62%) respectively. That the halogen had been introduced at C-5 was confirmed by comparison of ¹H-NMR spectra: the H-5 singlet at δ6.41 ppm present in (12) was not present in the spectra of(13a) and (13b). Unfortunately we were unable to isolate a tin derivative (14), for example treatment of (13a) with butyllithium then quenching with trimethyltin chloride, see Synthesis 1999, 615-620, gave a complex mixture which it was not possible to resolve. Attempted iodine-tin interchange by treatment of (13b) with hexamethylditin catalysed with Pd(PPh₃)₄ in dioxane afforded a mixture of (14) and (12) in a ratio of 7:3 but isolation of 14 by column chromatography failed.

Scheme 2

11 →ⁱ 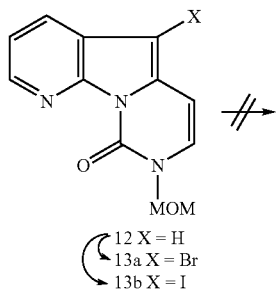

12 X = H
13a X = Br
13b X = I

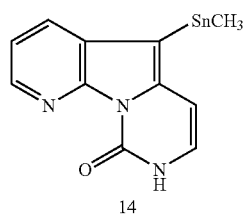

14 i: MOMCl, NaH, DMF, 0° C. (87%);
ii: NBS, CH₂Cl₂, 0° C. (80%);
ii: I₂, KOH, DMF, 0° C. (62%)

We changed the strategy for the coupling reaction using now the trimethylstannylpyrimidine (15) and the iodo-7-azaindole (13b). The preparation of pyrimidine (15), see Tetrahedron 1989, 45, 993-1006, was improved using Pd(OAc)₂ and PPh₃ in THF and by reduction of the amount TBAF and the reaction time in comparison with the previously described work.

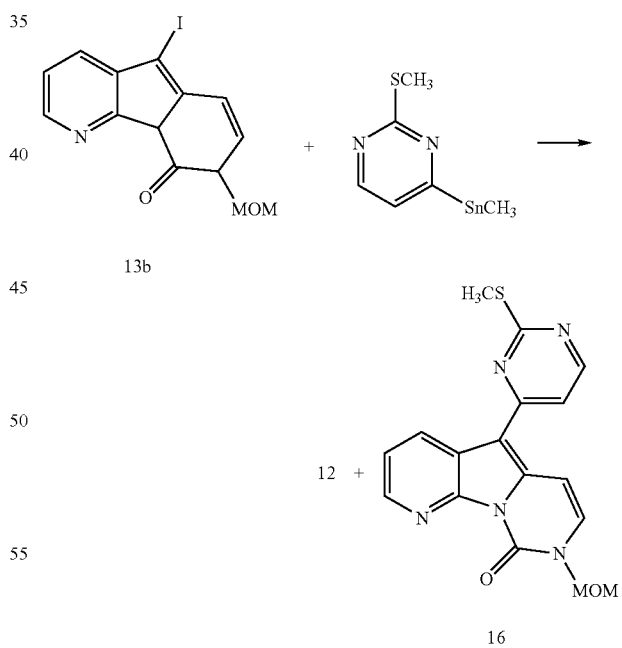

A solution of iododerivative (1 mmol), (15) (3 mmol), catalyst A or B, LiCL (3 mmol) in dioxane (20 ml) was refluxed for 5 hours. The sovent was evaporated and the residue purified by flash column chromatography. The coupling reaction between (13b) and (15) gave in all the experimental conditions a mixture of (12) and (16) which were impossible to separate (Table 1).

TABLE 1

Coupling reaction between (13b) and (15) in dioxane.

| (15)/(13b)[a] | Catal/Lig[b] | LiCl/CuI[c] | 16/12[d] | %[e] |
|---|---|---|---|---|
| 1.1 | A | 3/— | 2:1 | 56 |
| 1.2 | B | 3/— | 2:1 | 52 |
| 2 | B | 3/0.1 | 3:1 | 53 |

[a] molar ratio;
[b] A = Pd(PPh$_3$)$_4$, 0.1 equivalent; B = Pd$_2$(dba)$_3$ 0.1 equivalent and PPh$_3$ 0.2 equivalent;
[c] relative to 1 equivalent of 13b;
[d] ratio measured by $^1$H-NMR;
[e] yield of (16) calculated from the crude reaction mixture by $^1$H-NMR.

Because the difficulties of purification of (16) we tried with a new protecting group. The iodo compound (17) which differs of (13b) in the protecting group was synthesised by reaction of (11) with tosyl chloride and sodium hydride in DMF followed by iodination with NIS.

The coupling reaction between (17) and the trimethylstannylpyrimidine (15) afforded the tetracyclic compound (18) but only in 10% yield even using the best reaction conditions shown in Table 1 for the coupling between (13b) and (15).

Scheme 4. Synthesis of deoxyvariolin B

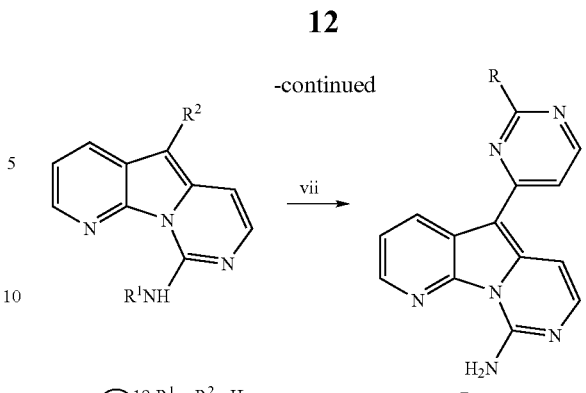

i: TsCl, NaH, DMF (40%);
ii, NIS. CHCl$_3$, rt (80%);
iii: 15, Pd$_2$(dba)$_3$, PPh$_3$, LiCl, CuI (10%);
iv: TMSCl, HMDSA, 2,6-lutidine;
v: NH$_3$, 150° C., 60 psi (30% two steps);
vi: Ac$_2$O, THF (75%);
vii: NIS. CHCl$_3$ (95%);
viii: iii then HCl—MeOH, (45%);
ix: MCPBA, CH$_2$Cl$_2$, 0° C. (90%);
x: NH$_4$OH, dioxane, 80° C. (90%)

Next approximation was the change of functionalization of the C ring by transformation of the pyrimidone (11) into the iodoaniidopyrimidine (20). The amino-derivative 19 was produced by O-silylation of (11) with TMSCl and hexanethyldisilazane (HMDSA) as silylating agent, followed by nucleophylic substitution with ammonia, see Lebgs Ann. Chem., 1975, 988-1002. Acylation of amine (19) and halogenation on the free position of the π-rich ring was proceeded in an excellent yield.

The heteroaryl coupling between (20) and (15) with the same reaction conditions and catalyst as before gave a mixture of acylated and deprotected amines which by methanolysis with dry HCl in methanol yielded the amine (21) in a 45% yield. Deoxyvariolin B (5) was prepared by substitution of the methylthio group of the new pyrimidine ring for an amino group. Oxidation of (21) using m-chloroperbenzoic acid followed by substitution of the resulting sulphone for an amino group using ammonium hydroxide afforded (5) in excellent yield, see Tetrrhedron 1989, 45, 993-1006 and Katrizly, A. R.; Rees, C. W. Comprehensive Heterocyclic Chemistry, Pergamon Press, Oxford, 1984, vol. 3, page 111.

A more general synthetic scheme is:

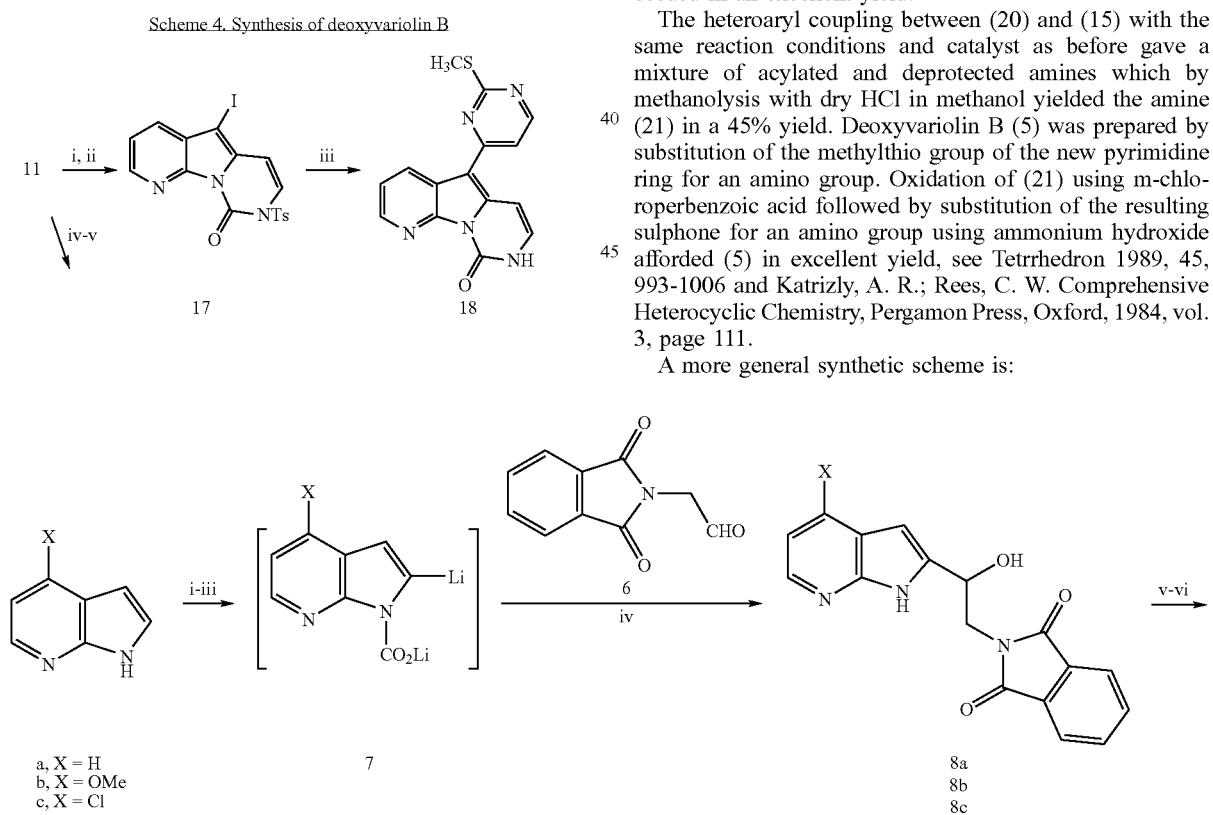

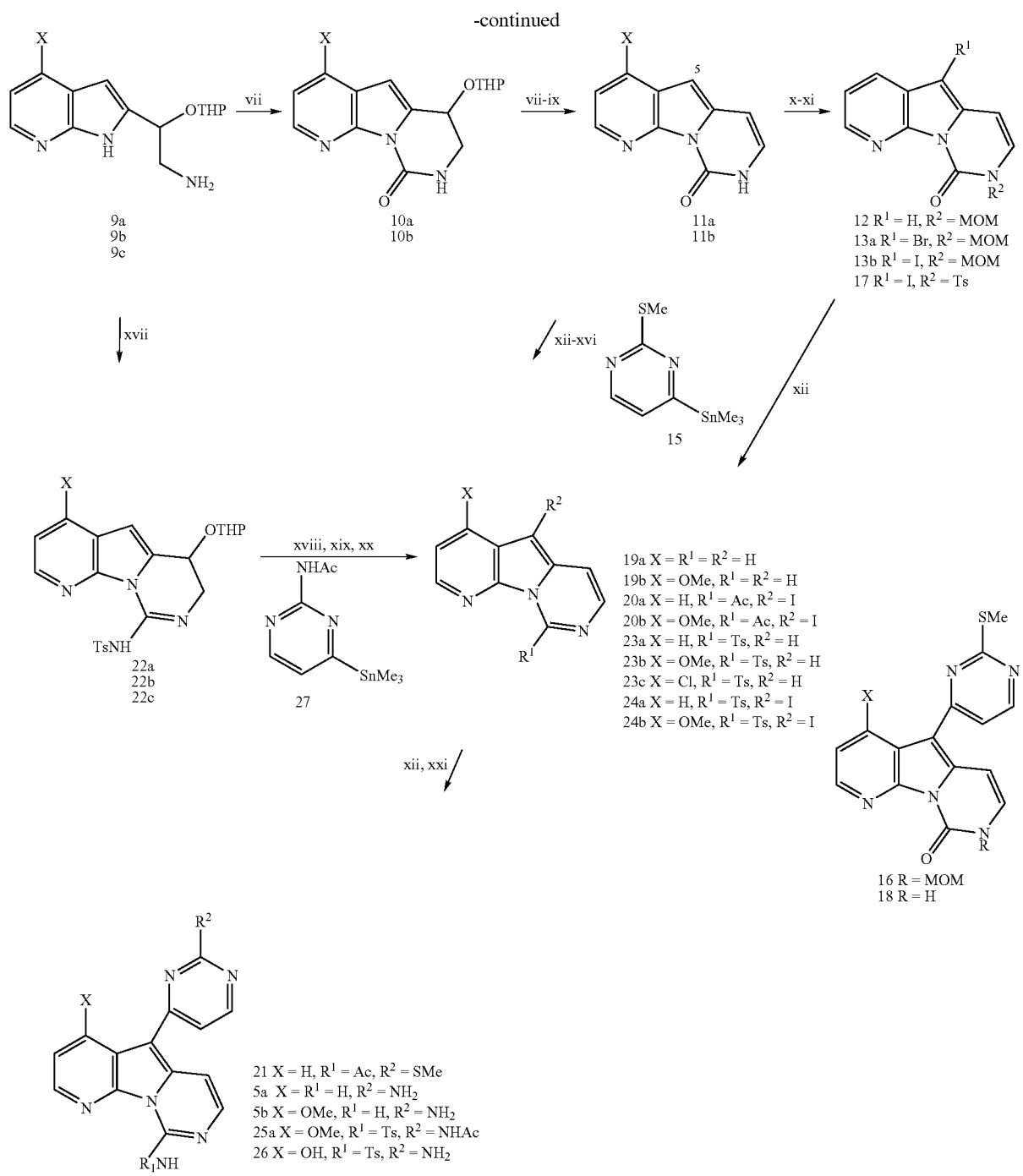

Reagents:
i: n-BuLi, THF, −78° C. to rt;
ii: CO₂, −78° C.;
iii: t-BuLi, THF, −78° C.;
iv: 6, THF, −78° C. to rt;
v: DHP, HCl, benzene, CHCl₃, Δ;
vi: NH₂NH₂.H₂O, EtOH, Δ;
vii: (Cl₃CO)₂CO, DIPEA, CH₂Cl₂, rt;
viii: 4N HCl, CH₂Cl₂;
ix: MsCl, TEA, CH₂Cl₂, 0° C.
x: MOMCl or TsCl, NaH, DMF, 0° C.;
xi: NBS/NIS, CH₂Cl₂, 0° C. or I₂, KOH, , 0° C.;
xii: 15, Pd₂(dba)₃, PPh₃, LiCl, CuI, dioxane, Δ;
xiii: TMSCl, HMDSA, lutidine, D;
xiv: NH₃, 150° C., 60 psi;
xv: Ac₂O, TBF, r.t;
xvi: NIS, CHCl₃, 0° C.;
xvii: TsN=CCl₂, DIPEA, CH₂Cl₂, r.t;
xviii: 4N HCl, CHCl₃, r.t;
xix: MsCl, TEA, CH₂Cl₂, rt;
xx: NIS, CHCl₃, −30° C.;
xxi: dry MeOH—HCl or 48% HBr, Δ.

The tricyclic comp. 11b (X=OMe) was prepared from 4-methoxy-7-azaindole, see *J. Heterocyclic Chem.* 1989, 26, 317, following the same way as the used for 11a. Transformation of 11b in 19b was produced with only a 22% yield by by O-silylation with trimethylsilyl chloride (TMSCl) and hexamethyldisilazane (HMDSA) hexamethyldisylazane followed by nucleophilic substitution with ammonia Acylation of 19b and iodination of the resulting acetyl derivative afforded the iodoacetamide 20b. The ¹HNMR of 20b shows two independent AB aromatic systems due to the H3-H4 and H7-H8 coupled protons. Palladium catalysed coupling between 20b and 2-acethylaminoftrimethylstannylpyrimidine (27) followed by acid treatment gave the O-methylvarioline B (5b). The stannylpyrimidine (27) was prepared with a 40% yield from 4-chloro-2-methanesulfonylpyrimidine, see *Heterocycles*, 1977, 8, 299, by nucleophylic substitution of the methanesulfonyl group with ammonia in i-PrOH followed by acylation with $Ac_2O$ and interchange halogen metal using hexamethylditin in dioxane with $Pd(PPh_3)_4$ as catalyst.

The pyrimidone ring formation was omited for improving the preparation of the tricyclic systems 19. Tricyclic compounds 22a-c were obtained from 9a-c by reaction with N-dichloromethylene4-methylbenzenesulfonamide, see *Chem. Ver.* 1966, 99, 1252, and DIPEA in $CH_2Cl_2$ followed by O-deprotection and dehydratation. N-Tosylderivatives 23 were prepared from 22 by acid catalysed O-deprotection followed by dehydratation in a simmilar way as described for the transformation of 10→11. Elimination of the N-tosyl protecting group in 23 was afforded using Na in ammonia or Na in naphthalene giving 19 with moderate yield.

Heteroaryl coupling reaction of 23 and the stannyl derivative 27 in a sinmmilar conditions as described previously gave 25 with a very good yield.

Deprotection of the N-acetyl could be produced by acid catalysed methanolysis with MeOH in HCl. Transformation of 25a→26 could be produced by treatment with HBr. Compound 26 is a new derivative of varioline B protected only in one nitrogen Several derivatives of varoline B have been obtained three of them with only one variation: 5a is the dehydroxyvarioline B, 5b is the methylvarioline B and 26 is the tosylvarioline B.

From 26 the elimination of the tosyl could be done in the same conditions as for 23 and will be obtained varioline B.

From 23c with a simmilar experimental procedure compound 25c would be produced and from that the derivatives in the pyridine ring.

Our previous experience indicate a previsible good results in the coupling between heteroaromatic tin derivatives and 13b, 17 and 24 giving the diversity of the $R^1$ in the general formula We have developed a versatile synthetic procedure which is potentially useful not only for the synthesis of this group of marine alkaloids but also for other derivatives of the natural products.

EXAMPLES OF THE INVENTION

Example 1

2-(1-Hydroxy-2-phthalimidoethyl)-7-azaindole (8a)

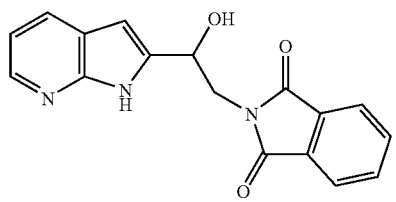

To a cooled (−78° C.) solution of 7-azaindole (7.6 g, 64 mmol) in dry THF (150 ml) n-BuLi (44 ml, 1.6 M in hexane) was added and the mixture was stirred for 10 min. Dry $CO_2$ was bubbled through the mixture for 40 min. The solvent was evaporated and the residue was dissolved in fresh dry THF (400 ml). The solution was cooled at −78° C. and t-BuLi (42 ml, 1.7 M in hexane) was added. The mixture was stirred for 20 min. A solution of ftalimidoacetaldehyde (14 g, 71 mmol) in THF (400 ml) was slowly added. After 1.5 h. the reaction was quenched with saturated aq. $NH_4Cl$ (100 ml) and the organic solvent evaporated. The mixture was dissolved in $CH_2Cl_2$ and washed with water. The organic solution was dried and evaporated. The mixture was purified by flash column chromatography. Elution with $CH_2Cl_2$/acetone (95/5) gave 7-azaindole (3.8 g, 50%) and with $CH_2Cl_2/MeOH(98/2)$ afforded 8a (8.7 g, 44%) as a white solid.

mp 231-232° C. ($CH_2Cl_2$/MeOH). IR (KBr) ν3200 (m, NH),1760 (s, C=O), 1704 (s, NCO), 1427 (m, C—N), 1395 (m, C—O). ¹H-NMR (DMSO-d⁶, 200 MHz) δ3.88 (dd, J 13.6 and 6.0, 1H, H₂'), 4.00 (dd, J 13.6 and 7.8, 1H, H₂'), 5.06 (ddd, J 7.8, 6.0 and 5.2, 1H, H1'), 5.83 (d, J 5.2, 1H, OH), 6.34 (d, J 1.8, 1H, H3), 6.99 (dd, J 8.0 and 4.8, 1H, H5), 7.81-7.88 (m, 4H, Phth), 7.89 (dd, J 8.0 and 1.4, 1H, H4), 8.14 (dd, J4.8 and 1.4, 1H, H6), 11.75 (brs, 1H, NH). ¹³C-NMR (DMSO-d⁶, 75 MHz) δ43.6 (t, C2'), 64.4 (d, C1'), 96.8 (d, C3), 115.4 (d, C5), 119.8 (s, C3a), 123.0 (d, Phth-β), 127.6 (d, C4), 131.6 (s, Phth-ipso), 134.3 (d, Phth-α), 140.8 (s, C2), 142.1 (d, C6), 148.6 (s, C7a), 167.7 (s, Phth-CO). MS (EI) m/z 308 (M+1, 6), 307 (M⁺, 25), 244 (8), 160 (43), 147 (phthalymide, 100), 119 (azaindole, 52). Analysis calculated for $C_{17}H_{13}N_3O_3$: C (66.44), H (4.26), N (13.67); found: C (65.11), H (4.26), N (13.37).

Example 2

2-(1-Hydroxy-2-phthalimidoethyl)-4-methoxy-7-azaindole (8b)

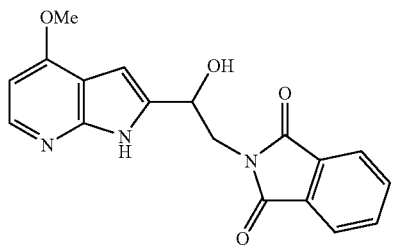

Following the previous methodology, from 4-methoxy-7-azaindole (3.55 g, 24 mmol) in THF (75 ml) n-BuLi (16.5 ml, 1.6 M in hexane), t-BuLi (16 ml, 1.7 M in hexane) and a solution of phthalimidoacetaldehyde (5 g, 26 mmol) in THF (100 ml) a crude mixture was obtained, which was purified by flash column chromatography. Elution with $CH_2Cl_2$/acetone (95/5) gave 4-methoxyazaindole (2.06 g, 58%) and with $CH_2Cl_2/MeOH(98/2)$ afforded 8b (3.68 g, 43%) as a white solid.

mp 225-226° C. ($CH_2Cl_2$/MeOH). IR (KBr) ν3500 (s, NH/OH), 1702 (s, C=O), 1594 (m), 1395 (m). ¹H-NMR (DMSO-d⁶, 300 MHz) δ 3.88 (s, 3H, Me), 3.86 (dd, J 13.8 and 6.0, 1H, H2'), 3.95 (dd, J 13.8 and 7.8, 1H, H2'), 5.00 (ddd, J7.8, 6.0 and 5.1, 1H, H1'), 5.73 (d, J 5.1, 1H, OH), 6.30 (d, J 1.8, 1H, H3), 6.58 (d, J 5.4, 1H, H5), 7.83 (m, 4H, Phth), 8.02 (d, J 5.4, 1H, H6), 11.65 (br, 1H, NH). ¹³C-NMR (DMSO-d⁶, 75 MHz) δ 43.6 (t, C2'), 55.3 (q, Me), 64.2 (d, C1'), 94.0 (d, C5), 97.8 (d, C3), 109.5 (s, C3a), 123.0 (d, Phth-P), 131.6 (s, Phth-ipso), 134.3 (d, Phth-α), 138.1 (s, C2), 144.2 (d, C6), 150.3 (s, C7a*), 158.5 (s, C4*), 167.7 (s, Phth-CO). MS (EI) m/z 338 (M+1, 4), 337 (M⁺, 20), 319 (M-H₂O, 44), 177 (100). Analysis calculated for $C_{18}H_{15}N_3O_4 \cdot 1/4H_2O$: C (63.25), H (4.57), N (12.29); found: C (63.32), H (4.54), N (12.07).

Example 3

4-Chloro-2-(1-Hydroxy-2-phthalimidoethyl)-7-azaindole (8c)

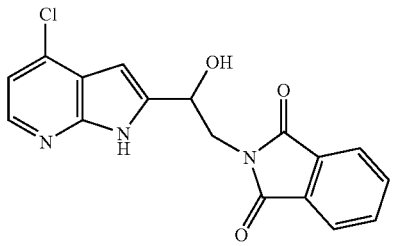

Following the previous methodology, from 4-Chloro-7-azaindole (5 g, 33 mmol) in THF (100 ml) n-BuLi (20 ml, 1.6 M in hexane), t-BuLi (20 ml, 1.7 M in hexane) and a solution of ftalimidoacetaldehyde (7.5 g, 39 mmol) in THF (140 ml) a crude mixture was obtained, which was purified by flash column chromatography. Elution with $CH_2Cl_2$/acetone (95/5) gave 4-chloroazaindole (4 g, 80%) and with $CH_2Cl_2$/MeOH(98/2) afforded 8c (1.5 g, 12%) as a white solid.

$^1$H-NMR (DMSO-d$^6$, 200 MHz) δ 3.86 (m, 1H, H2'), 3.95 (m, 1H, H2'), 5.01 (m, 1H, H1'), 5.92 (d, J 5.2, 1H, OH), 6.41 (s, 1H, H3), 7.14 (d, J 5.6, 1H, H5), 7.84 (m, 4H, Phth), 8.11 (d, J5.6, 1H, H6), 11.75 (br, 1H, NH). $^{13}$C-NMR (DMSO-d$^6$, 75 MHz) δ 43.6 (t, C2'), 64.3 (d, C1'), 94.9 (d, C3), 115.3 (d, C5), 118.7 (s, C3a), 123.0 (d, Phth-β), 131.6 (s, Phth-ipso), 133.3 (s, C2), 134.3 (d, Phth-α), 142.2 (s, C4), 142.8 (d, C6), 49.2 (s, C7a), 167.7 (s, Phth-CO). MS (EI) m/z 342 (M+1, 4), 341 (M$^+$, 20), 323 (M-H$_2$O, 44), 177 (100).

Example 4

2-[2-Phthalimido-1-(2,3,5,6-tetrahydropyran-2-yl)oxyethyl]-7-azaindole

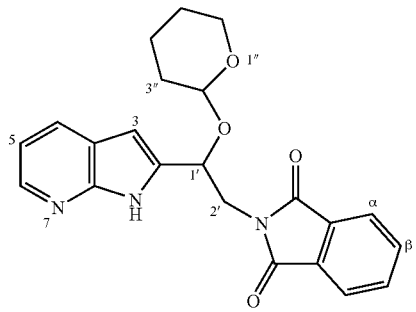

To a solution of 8a (10.2 g, 33 mmol) in CHCl$_3$ (11) 6N HCl in dry benzene (180 ml) was added. To the mixture 2,3-dihydropyrane (46 ml, 330 mmol) was added. The reaction was refluxed for 7 h. After cooling the mixture was washed with saturated aq. NaHCO$_3$, dried and evaporated. The mixture was purified by flash column chromatography. Elution with $CH_2Cl_2$/MeOH (97/3) gave 2-[2-phthalmido-1-(2,3,5,6-tetrahydropyran-2-yl)oxy-ethyl]-7-azaindole (10.8 g, 87%) as a diastereomeric mixture (1:1) as a white solid.

IR (film) ν1717 (s, C=O), 1390 (m, C—O), 1026 (m, C—O). $^1$H-NMR (CDCl$_3$, 200 MHz) δ 1.30-1.80 (m, 6H, H3", H4" and H5"), 3.25-3.45 (m, 2H, H2'), 3.80, 3.98, 4.22 and 4.38 (m, dd, J 14.0 and 4.4, dd, J 14.8 and 2.0 and dd, J 14.0 and 9.4, 2H, H6"), 4.58 and 4.72 (dd, J 3.2 and 2.8 and dd, J 3.4 and 3.0, 1H, H2"), 5.30 and 5.39 (dd, J8.4 and 5.2 and dd, J9.2 and 4.0, 1H, H1'), 6.47 and 6.51 (d, J 1.8 and d, J 1.8, 1H, H3), 7.08 and 7.15 (dd, J 8.2 and 4.8 and dd, J 8.2 and 5.2, 1H, H5), 7.69 (m, 2H, Phth-β, 7.86 (m, 2H, Phth-α), 7.86 (m, 1H, H4), 8.43 and 8.63 (dd, J4.8 and 1.6 and dd, J 5.0 and 1.7, 1H, H7), 10.8 and 12.5 (br, 1H, NH). $^{13}$C-NMR (CDCl$_3$, 50 MHz) δ 18.8 and 19.9 (t, C3"*), 25.0 and 25.2 (t, C4"*), 30.2 and 30.8 (t, C5"*), 41.6 and 42.8 (t, C6"), 61.8 and 63.6 (t, C2'), 69.3 and 71.7 (d, C1'), 95.5 and 97.9 (d, C2"), 100.3 and 100.8 (d, C3), 115.9 (d, C5), 120.6 and 120.7 (s, C3a), 123.2 and 123.4 (d, Phth-β), 128.7 and 128.8 (d, C4), 131.8 and 132.0 (s, Phth-ipso), 133.9 and 134.0 (d, Phth-α), 136.5 and 137.8 (s, C2), 143.1 (d, C6), 148.7 and 149.2 (s, C7a), 168.1 (s, Phth-CO). MS (EI) m/z 391 (M$^+$, 1), 307 (M-THP, 9), 147 (38), 85 (100). Analysis calculated for $C_{22}H_{21}N_3O_4 \cdot 1/2H_2O$: C (65.99), H (5.54), N (10.49); found: C (66.02), H (5.80), N (10.28).

Example 5

4Methoxy-2-[2-phthalimido-1-(2,3,5,6-tetrahydropyran-2-yl)oxyethyl]-7-azaindole

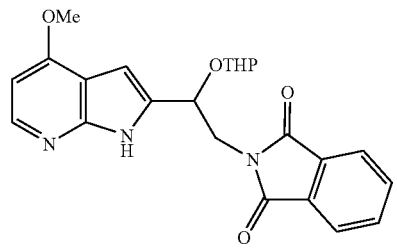

Following the same procedure as for 2-[2-Phthalimido-1-(2,3,5,6-tetrahydropyran-2-yl)oxyethyl]-7-azaindole. From 8b (3.8 g, 11 mmol) in CHCl$_3$ (350 ml), 6N HCl in benzene (35 ml) and 2,3-dihydropyrane (10 ml, 110 mmol). 4Methoxy-2-[2-phthalimido-1-(2,3,5,6-tetrahydropyran-2-yl)oxyethyl]-7-azaindole (3.07 g, 65%) as a diastereomeric mixture (1:1) was obtained.

IR (film) ν1714 (s, C=O), 1392 (m, C—O), 1026 (m, C—O). $^1$H-NMR (CDCl$_3$, 300 MHz) δ 1.30-1.80 (m, 6H, H3", H4" and H5"), 3.25-3.45 (m, 2H, H2'), 3.99 and 4.01 (s, 3H, OMe), 3.96, 4.08, 4.28 and 4.39 (dd, J 13.5 and 3.9, dd, J 13.8 and 4.6, dd, J 13.8 and 8.5 and dd, J 13.5 and 9.6, 2H, H6"), 4.57 and 4.73 (brt, J 3.2 and brt, J 3.4, 1H, H12"), 5.25 and 5.33 (dd, J 6.9 and 2.4 and dd, J 9.9 and 4.1, 1H, H1'), 6.54 and 6.58 (brs and brs, 1H, H3), 6.56 and 6.62 (d, J 5.7 and d, J 5.7, 1H, H5), 7.68 (m, 2H, Phth-β, 7.83 (m, 2H, Phth-α), 8.38 and 8.57 (d, J 5.7 and d, J 5.7, 1H, H7), 11.7 (br, 1H, NH). $^{13}$C-NMR (CDCl$_3$, 50 MHz) δ 18.9 and 19.5 (t, C3"*), 25.0 and 25.3 (t, C4"*), 30.2 and 30.7 (t, C5"*), 42.0 and 43.0 (t, C6"), 55.4 (q, MeO), 61.7 and 62.9 (t, C2'), 69.4 and 71.5 (d, C1'), 94.4 and 95.3 (d, C2"), 97.7 (d, C5), 97.8 and 100.1 (d, C3), 110.5 (s, C3a), 123.1 and 123.2 (d, Phth-β), 132.1 and 132.1 (s, Phth-ipso), 133.8 and 133.9 (d, Phth-α), 134.0 and 135.2 (s, C2), 144.9 and 145.1 (d, C6), 150.6 and 151.1 (s, C7a*), 159.8 (s, C4*), 168.1 (s, Phth-CO). MS (EI) m/z 422 (M+1, 2), 421 (M$^+$, 4), 337 (M-THP, 15), 177 (100). HRMS m/z calculated for $C_{23}H_{23}N_3O_5$: 421.1637; found: 421.1625.

Example 6

4Chloro-2-[2-phthalimido-1-(2,3,5,6-tetrahydropyran-2-yl)0xyethyl]-7-azaindole

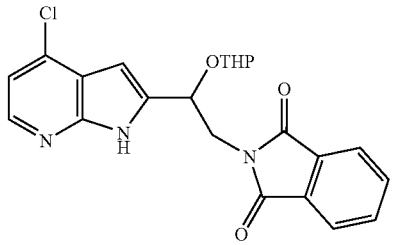

Following the same procedure as for 2-[2-Phthalimido-1-(2,3,5,6-tetrahydropyran-2-yl)oxyethyl]-7-azaindole, from 8c (1.3 g, 3.8 mmol) in CHCl$_3$ (50 ml), 6N HCl in benzene (5 ml) and 2,3-dihydropyrane (1.7 ml, 19 mmol), 4-chloro-2-[2-phthalimido-1-(2,3,5,6-tetrahydropyran-2-yl)oxyethyl]-7-azaindole (1.0 g, 63%) as a diastereomeric mixture (1:1) was obtained.

$^1$H-NMR (CDCl$_3$, 200 MHz) δ 1.30-1.80 (m, 6H, H3", H4" and H5"), 3.25-3.45 (m, 2H, H2'), 3.96-4.39 (m, 2H, H6"), 4.58 and 4.72 (m, 1H, H2"), 5.30 and 5.40 (dd, J 8.4 and 4.4 and dd, J 9.2 and 4.0, 1H, H1'), 6.58 and 6.63 (d, J 2.2 and d, J 2.2, 1H, H3), 7.13 and 7.20 (d, J 5.2 and d, J 5.2, 1H, H5), 7.70 (m, 2H, Phth-β), 7.86 (m, 2H, Phth-α), 8.35 and 8.55 (d, J 5.2 and d, J 5.2, 1H, H7), 11.7 (br, 1H, NH). $^{13}$C-NMR (CDCl$_3$, 50 MHz) δ 18.9 and 19.5 (t, C3"*), 25.0 and 25.3 (t, C4"*), 30.2 and 30.8 (t, C5"*), 41.8 and 42.9 (t, C6"), 61.9 and 63.5 (t, C2'), 69.2 and 71.6 (d, C1') 95.5 and 96.4 (d, C2"), 98.8 and 100.7 (d, C3), 116.1 (d, C5), 116.3 (s, C3a), 123.1 and 123.3 (d, Phth-β), 131.7 and 132.0 (s, Phth-ipso), 133.8 and 133.9 (d, Phth-α), 134.0 (s, C2), 143.2 and 143.3 (d, C6). MS (EI) m/z 426 (M+1, 2), 425 (M$^+$, 5), 341 (M-THP, 14), 177 (100).

Example 7

2-[2-Amino-1-(2,3,5,6-tetrahydropyran-2-yl)oxyethyl]-7-azaindole (9a)

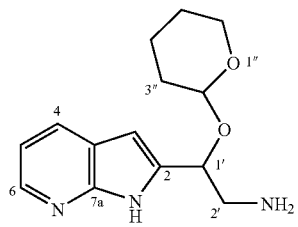

To a solution of 2-[2-Phthalimido-1-(2,3,5,6-tetrahydropyran-2-yl)oxyethyl]-7-azaindole (10.2 g, 26 mmol) in EtOH (630 ml) NH$_2$NH$_2$.H$_2$O (1.53 ml, 31 mmol) was added. The mixture was refluxed for 3 h. The solvent was evaporated, the residue dissolved in CH$_2$Cl$_2$ and washed with saturated aq. NaHCO$_3$. The aqueous layer was extracted three times with CH$_2$Cl$_2$. The organic solutions were evaporated together to obtain a diastereomeric mixture (1:1) of 9a (6.72 g, 100%) as a light orange solid.

IR (film) ν3200 (m, NH), 1421 (m, C—N), 1022 (m, C—O). $^1$H-NMR (CDCl$_3$, 200 MHz) δ 1.40-1.90 (m, 6H, H3", H4" and H5"), 3.20 (m, 2H, H2'), 3.48 and 3.90 (m, 1H, H6"), 4.60 and 4.85 (brt, J 3.5 and m, 1H, H2") 4.85 and 4.97 (m and brt, J 5.7, 1H, H1'), 6.32 and 6.43 (s, 1H, H3), 7.03 and 7.07 (dd, J 6.6 and 4.8 and dd, J 6.6 and 5.0, 1H, H5), 7.85 and 7.90 (dd, J 6.6 and 1.4, 1H, H4), 8.29 and 8.36 (dd, J 4.8 and 1.4 and dd, J 5.0 and 1.4, 1H, H7), 10.9 and 12.5 (br, NH). $^{13}$C-NMR (CDCl$_3$, 75 MHz) δ 19.7 and 20.0 (t, C3"*), 25.1 and 25.3 (t, C4"*), 30.6 and 30.9 (t, C5"*), 45.3 and 47.3 (t, C6"), 62.9 and 63.5 (t, C2'), 73.4 and 75.5 (d, C1'), 96.1 and 97.3 (d, C2"), 99.8 and 99.9 (d, C3), 115.6 (d, C5), 120.7 (s, C3a), 128.4 and 128.5 (d, C4), 138.3 and 139.0 (s, C2), 142.2 and 142.3 (d, C6), 148.5 and 149.0 (s, C7a). MS (CI CH$_4$) m/z 263 (M+1,15), 262 (M$^+$, 100). HRMS m/z calculated for C$_{14}$H$_{19}$N$_3$O$_2$.H: 262.1555; found: 262.1557.

Example 8

2-[2-Amino-1-(2,3,5,6-tetrahydropyran-2-yl)oxyethyl]-4-methoxy-7-azaindole (9b)

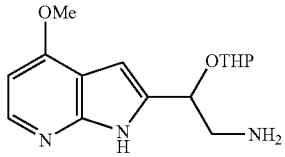

Following the same procedure as for 9a. From 4-Methoxy-2-[2-phthalimido-1-(2,3,5,6-tetrahydropyran-2-yl)oxyethyl]-7-azaindole (2.9 g, 10 mmol) in EtOH (100 ml) and NH$_2$NH$_2$.H$_2$O (420 µl, 15 mmol). After a reaction time of 3 h. a diastereomeric mixture (1:1) of 9b (1.9 g, 95%) was obtained.

IR (film) ν3150 (m, NH), 1590 (m, C=C), 1329 (m, C—N), 1114 (m, C—O). $^1$H-NMR (CDCl$_3$, 200 MHz) δ 1.40-1.90 (m, 6H, H3"-H5"), 3.19 (m, 2H, H2'), 3.48 and 3.90 (m, 1H, H6"), 3.99 and 4.00 (s, 3H, MeO), 4.60 and 4.85 (m, 1H, H2") 4.85 and 4.97 (m and brt, J 5.7, 1H, H1'), 6.42 and 6.51 (s, 1H, H3), 6.51 and 6.55 (d, J 5.4, 1H, H5), 8.23 and 8.30 (d, J 5.4, 1H, H7). $^{13}$C-NMR (CDCl$_3$, 75 MHz) δ 20.0 (t, C3"*), 25.2 and 25.4 (t, C4"*), 30.7 and 30.9 (t, C5"*), 45.4 and 47.4 (t, C6"), 55.4 and 55.5 (q, MeO), 62.9 and 63.4 (t, Q2'), 73.5 and 75.5 (d, C1'), 94.7 and 96.1 (d, C2"*), 97.1 and 99.6 (d, C3), 97.6 and (d, C5), 110.5 (s, C3a), 135.8 and 136.5 (s, C2), 144.3 and 144.4 (d, C6), 150.3 and 151.3 (s, C4*), 159.4 and 159.5 (s, C7a*). MS (CI, CH$_4$) m/z 291 (M$^+$, 2), 262 (M-CH$_2$NH$_3$, 12), 190 (M-THPO, 8), 177 (100).

Example 9

2-[2-Amino-1-(2,3,5,6-tetrahydropyran-2-yl)oxyethyl]4-chloro-7-azaindole (9c)

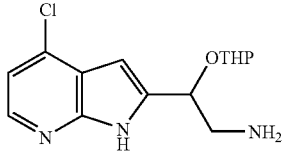

Following the same procedure as for 9a, from 4-Chloro-2-[2-phthalimido-1-(2,3,5,6-tetrahydropyran-2-yl)oxyethyl]-7-azaindole (950 mg, 2.2 mmol) in EtOH (50 ml) and NH$_2$NH$_2$.H$_2$O (250 µl, 4.4 mmol). After a reaction time of 3 h. a diastereomeric mixture (1:1) of 9c (640 mg, 97%/o) was obtained.

$^1$H-NMR (CDCl$_3$, 200 MHz) δ 1.40-1.90 (m, 6H, H3"-H5"), 3.19 (m, 2H, H2'), 3.50 and 3.95 (m, 1H, H6"), 4.60 and 4.85 (m, 1H, H2") 4.85 and 4.97 (brt, 1H, H1'), 6.46 and 6.54 (s, 1H, H3), 7.07 and 7.10 (d, J 5.4, 1H, H5), 8.19 and 8.25 (d, J 5.4, 1H, H7). $^{13}$C-NMR (CDC13, 75 MHz) δ 19.8 and 20.1 (t, C3"*), 25.1 and 25.3 (t, C4"*), 30.6 and 30.9 (t, C5"*), 45.2 and 47.1 (t, C6"), 63.1 and 63.7 (t, C2'), 73.1 and 75.1 (d, C1'), 96.0 and 96.4 (d, C2"*), 98.3 and 100.2 (d, C3), 115.8 (d, CS), 120.1 and 120.4 (s, C4), 135.6 and 135.8

(s, C4), 139.1 and 139.8 (s, C3a), 142.4 and 142.5 (d, C6), 148.9 and 149.5 (s, C7a). MS (CI, CH$_4$) m/z 295 (M$^+$, 2), 266 (M-CH$_2$NH$_3$, 12), 194 (M-THPO, 8), 177 (100).

Example 10

6,7,8,9-Tetrahydro6-(2,3,5,6-tetrahydropyran-2-yl) oxypyrido[3',2':4,5]pyrrolo[1,2-c]pyrimidin-9-one (10a)

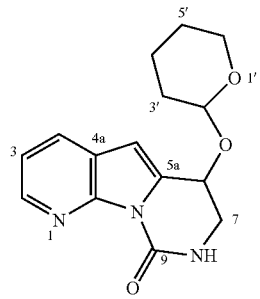

A solution of 9a (7.4 g, 28 mmol) and DIPEA (5 ml, 28 mmol) in CH$_2$Cl$_2$ (300 ml) was slowly added to a solution of triphosgene (2.82 g, 10 mmol) in CH$_2$Cl$_2$ (740 ml) and the mixture was stirred at room temperature for 30 min. The organic mixture was washed with saturated aq. NH$_4$Cl and with water. The organic solution was dried and evaporated to give a diastereomeric mixture (1:1) of 10a (6.06 g, 76%).

IR (KBr) ν3252 (m, NH), 1716 (s, C=O), 1407 (m, C—N), 1302 (m, C—O). $^1$H-NMR (CDCl$_3$, 200 MHz) δ 1.40-1.80 (m, 6H, H3', H4' and H5'), 3.454.00 (m, 2H, H7 and H6'), 3.90 (m, 2H, H7 and H6'), 4.71 and 4.94 (m, 1H, H2'), 5.04 and 5.10 (dd, J 3.2 and 3.0 and t, J 4.4, 1H, H6), 6.56 and 6.59 (s, 1H, H5), 6.79 and 7.00 (br, 1H, NH), 7.20 and 7.22 (dd, J 7.6 and 4.8 and dd, J 8.0 and 4.8, 1H, H3), 7.89 and 7.93 (dd, J 7.6 and 1.8 and dd, J 8.0 and 1.8, 1H, H4), 8.54 and 8.57 (dd, J 4.8 and 1.8 and dd, J 4.8 and 1.4, 1H, H2). $^{13}$C-NMR (CDCl$_3$, 50 MHz) δ 18.9 and 19.3 (t, C4'), 25.3 and 25.4 (t, C5'), 30.1 and 30.4 (t, C3'), 43.5 and 45.3 (t, C6'), 62.2 and 62.6 (t, C7), 63.2 and 64.3 (d, C6), 95.7 and 96.7 (d, C2'), 102.3 and 103.7 (d, C5), 118.6 (d, C3), 121.3 and 121.7 (s, C4a), 129.1 and 129.2 (d, C4), 133.5 and 136.1 (s, C5a), 145.2 and 145.6 (d, C2), 148.0 and 148.1 (s, C10a), 149.8 and 150.2 (s, C9). MS (CI, CH$_4$) m/z 289 (M+1, 6), 288 (M$^+$, 25), 204 (M-THP, 23), 85 (THP, 100). HRMS m/z calculated for C$_{15}$H$_{17}$N$_3$O$_3$.H: 288.1348; found: 288.1352.

Example 11

6,7,8,9-Tetrahydro-6(2,3,5,6-tetrahydropyran-2-yl) oxy4-methoxy-pyrido[3',2':4,5]-Pyrrolo[1,2-c]pyrimidin-9-one (10b)

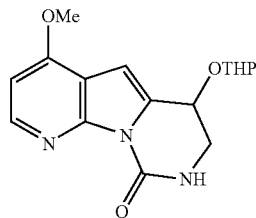

Following the same procedure as for 10a, from triphosgene (20 mg, 0.07 mmol) in CH$_2$Cl$_2$ (3 ml), 9b (58 mg, 0.20 mmol) and DIPEA (34 µl, 0.20 mmol) in CH$_2$Cl$_2$ (3 ml). Reaction time 30 min. at room temperature. The crude mixture was purified by flash column chromatography. Elution with CH$_2$Cl$_2$/MeOH (98/2) gave a diastereomeric mixture (1:1) of 10b (40 g, 63%).

IR (KBr) ν3258 (m, NH), 1714 (s, C=O), 1566 (m, C=N), 1290 (m, C—O). $^1$H-NRM (CDCl$_3$, 200 MHz) δ 1.40-1.80 (m, 6H, H3', H4' and H5'), 3.45 and 3.95 (m, 2H, H6'), 3.65 and 3.75 (m, 2H, H7), 4.00 (s, 3H, MeO), 4.67 and 4.94 (m, 1H, H2'), 4.99 and 5.07 (m, 1H, H6), 6.20 and 6.30 (br, 1H, NH), 6.65 and 6.66 (s, 1H, H5), 6.69 (d, J 5.9, 1H, H3), 8.44 and 8.46 (d, J 5.9, 1H, H2). $^{13}$C-NMR (CDCl$_3$, 50 MHz) δ 18.7 and 19.4 (t, C4'), 25.3 and 25.4 (t, C5'), 30.1 and 30.3 (t, C3'), 43.5 and 45.3 (t, C6'), 61.9 and 62.6 (t, C7), 62.9 and 63.9 (d, C6), 95.5 and 96.2 (d, C2'), 99.6, 100.6 and 101.1 (d, C3 and C5), 130.9 (s, C5a), 147.3 and 147.7 (d, C2), 149.9 and 150.3 (s, C10a or C4), 159.7 (s, C9). MS (EI) m/z 318 (M+1, 2), 317 (M$^+$, 28), 233 (22), 217 (66), 216 (65), 177 (100), 85 (THP, 100). HRMS m/z calculated for C$_{16}$H$_{19}$N$_3$O$_4$: 317.1376; found: 317.1383.

Example 12

6,7,8,9-Tetrahydro6-hydroxypyrido[3',2':4,5]pyrrolo [1,2-c]pyrimidin-9-one

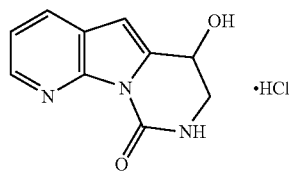

To a solution of 10a (6 g, 21 mmol) in CH$_2$Cl$_2$ (400 ml) 4N aq. HCl (400 ml) was added. After 45 min. stirring at room temperature the two layers were separated. The organic solution was extracted with 4N aq. HCl. The aqueous solution was filtered and evaporated to obtain 6,7,8,9-Tetrahydro-6-hydroxypyrido[3',2':4,5]pyrrolo[1,2-c]pyrimidin-9one (5 g, 100%) as hydrochloride salt as a light orange solid.

6,7,8,9-Tetrahydro-6-hydroxypyrido[3', 2':4,5]pyrrolo[1,2-c]pyrimidin-9-one hydrochloride IR (KBr) ν3500 (s, OH), 1721 (s, C=O), 1638 (m, C=C), 1503 (m, C=N). $^1$H-NMR (CD$_3$OD, 300 MHz) δ 3.61 (dd, J 13.0 and 5.0, 1H, H7), 3.77 (dd, J 13.0 and 4.0, 1H, H7), 5.23 (dd, J 5.0 and 4.0, 1H, H6), 7.05 (s, 1H, H5), 7.86 (dd, J 8.0 and 6.0, 1H, H3), 8.56 (dd, J 6.0 and 1.2, 1H, H2), 8.86 (dd, J 8.0 and 1.2, 1H, H4). $^{13}$C-NMR (CD$_3$OD, 75 MHz) δ 45.8 (t, C7), 59.6 (d, C6), 101.9 (d, C5), 119.0 (d, C3), 127.1 (s, C4a), 124.3 (d, C4), 137.4 (s, C5a), 139.4 (d, C2), 141.9 (s, C10a), 149.0 (s, C9). MS (CI, NH$_3$) m/z 205 (M+1, 3), 204 (M$^+$, 4), 180 (100), 163 (50), 130 (90). HRMS m/z calculated for C$_{10}$H$_{10}$N$_3$O$_3$: 204.0773; found: 204.0772.

A solution of 6,7,8,9-Tetrahydro-6-hydroxypyrido[3',2':4, 5]pyrrolo[1,2-c]pyrimidin-9-one hydrochloride salt in saturated aq. Na$_2$CO$_3$ was extracted in continuous with CH$_2$Cl$_2$ to give the conjugated base.

6,7,8,9-Tetrahydro-6-hydroxypyrido[3',2':4,5]pyrrolo [1,2-c]pyrimidin-1-9-one

IR (KBr) ν3400 (m, NH/OH), 1707 (s, C=O), 1468 (m, C—N), 1408 (m, C—N), 1297 (m, C—O). $^1$H-NMR (DMSO-d$^6$, 300 MHz) δ 3.27 (m, 1H, H7), 3.42 (m, 1H, H7), 4.90 (dd, J 9.3 and 5.1, 1H, H6), 5.88 (d, J 5.1, 1H, OH), 6.54 (s, 1H, H5), 7.21 (dd, J 7.4 and 4.2, 1H, H3), 7.88 (br, 1H, NH), 7.99 (brd, J 7.4, 1H, H2), 8.30 (brd, J 4.2, 1H, H4). $^{13}$C-NMR (DMSO-d$^6$, 75 MHz) δ 41.0 (t, C7), 55.7 (d, C6), 95.4 (d, C5), 113.8 (d, C3), 116.7 (s, C4a), 124.2 (d, C4), 135.4 (s, C5a), 139.3 (d, C2), 142.9 (s, C10a*), 143.8 (s, C9*).

Example 13

6,7,8,9-Tetrahydro-6-hydroxy4-methoxypyrido[3',2':4,5]pyrrolo[1,2-c]pyrimidin-9-one

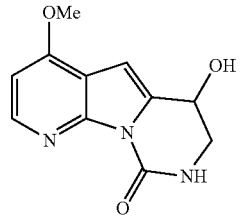

To a solution of 10b (25 mg, 0.08 mmol) in CH$_2$Cl$_2$ (5 ml) 4N aq. HCl (5 ml) was added and the mixture was stirred at room temperature for 45 min. The organic solution was separated and extracted with 4N aq. HCl. The aqueous solution was filtered and evaporated to obtain 6,7,8,9-Tetrahydro-6-hydroxy-4-methoxypyrido[3',2':4,5]pyrrolo[1,2-c]pyrimidin-9-one (20 mg, 95%) as hydrochloride salt as a light orange solid.

IR (film) ν3244 (m, NH), 1718 (s, C=O), 1627 (s, NCO), 1505 (m, C=N), 1298 (m, C—O). $^1$H-NMR (CD$_3$OD, 200 MHz) δ 3.56 (dd, J 13.6 and 4.8, 1H, H7), 3.71 (dd, J 13.6 and 3.6, 1H, H7), 4.29 (s, 3H, MeO), 5.11 (dd, J 4.8 and 3.6, 1H, H6), 6.91 (s, 1H, H5), 7.40 (d, J 6.9, 1H, H3), 8.42 (d, J 6.9, 1H, H2). $^{13}$C-NMR (CD$_3$OD, 75 MHz) δ 48.9 (t, C7), 60.5 (q, Me), 62.3 (d, C6), 101.7 (d, C5), 105.5 (d, C3), 117.4 (s, C4a), 137.0 (s, C5a), 140.6 (d, C2), 141.4 (s, C10a), 151.9 (s, C9), 169.0 (s, C4). MS (EI) m/z 234 (M+1, 12), 233 (M$^+$, 77), 215 (M-H$_2$O, 17), 55 (100). HRMS m/z calculated for C$_{11}$H$_{11}$N$_3$O$_3$: 233.0800; found: 233.0813.

Example 14

8,9-Dihydropyrido[3',2':4,5]pyrrolo[1,2-c]pyrimidin-9-one (11a)

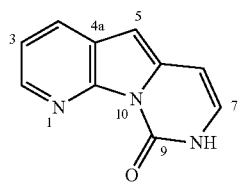

To a cooled (0° C.) solution of 6,7,8,9-Tetrahydro-6-hydroxypyrido[3',2':4,5]pyrrolo[1,2-c]pyrimidin-9-one (1 g, 4.2 mmol) and TEA (1.74 ml, 13 mmol) in CH$_2$Cl$_2$ (200 ml) MsCl (320 µl, 4.2 mmol) was dropwise added. The reaction mixture was stirred for 30 min. at the same temperature and the organic solution was washed with saturated aq. NH$_4$Cl and with water. The organic solution was dried and evaporated to obtain 11a (730 mg, 95%), as a white solid without further purification mp 265-266° C. (MeOH). IR (KBr) ν3424 (m, NH), 1721 (s, C=O), 1691 (m, NCO), 1633 (m, C=C), 1408 (m, C=N), 1380 (m), 1303 (m). $^1$H-NMR (DMSO-d$^6$, 300 MHz) δ 6.50 (d, J 7.4, 1H, H6), 6.60 (s, 1H, H5), 6.97 (dd, J 7.4 and 5.3, 1H, H7), 7.37 (dd, J 8.0 and 4.7, 1H, H3), 8.08 (dd, J 8.0 and 1.7, 1H, H4), 8.39 (dd, J 4.7 and 1.7, 1H, H2), 10.81 (brd, J 5.3, 1H, NH). $^{13}$C-NMR (DMSO-d$^6$, 75 MHz) δ 94.9 (d, C5), 98.0 (d, C6), 119.8 (d, C3), 123.1 (s, C4a), 127.5 (d, C4), 128.0 (d, C7), 137.0 (s, C5a), 142.5 (d, C2), 145.6 (s, C10a*), 146.7 (s, C9*). MS (EI) m/z 186 (M+1, 18), 185 (M$^+$, 15), 157 (M-CO, 10) (CI NH$_3$) m/z 204 (M+18, 12), 187 (M+2, 14), 186 (M+1, 100), 109 (48). HRMS m/z calculated for C$_{10}$H$_7$N$_3$O: 185.0589, found: 185.0593.

Example 15

8,9-Dihydro4-methoxypyrido[3',2':4,5]pyrrolo[1,2-c]pyrimidin-9ona (11b)

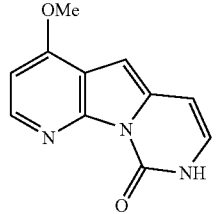

Following the same procedure for 11a, from 6,7,8,9-tetrahydro-6-hydroxy4-methoxypyrido[3',2':4,5]pyrrolo[1,2-c]pyrimidin-9-one (113 mg, 0.42 mmol), TEA (195 µl, 1.25 mmol) and MsCl (32 µl, 0.42 mmol) in CH$_2$Cl$_2$ (20 ml). Reaction time 30 min. 11b (74 mg, 85%) was obtained as a white solid without further purification.

IR (KBr) ν3380 (m, NH), 1721 (s, C=O), 1693 (m, NCO), 1633 (m, C=C), 1500 (m, C=N), 1294 (m, C—O). $^1$H-NMR (DMSO-d$^6$, 500 MHz) δ 3.98 (s, 3H, Me), 6.44 (d, J 7.5, 1H, H6), 6.54 (s, 1H, H5), 6.89 (dd, J 7.5 and 2.0, 1H, H7), 6.96 (d, J 5.5, 1H, H3), 8.26 (d, J 5.5, 1H, H2). $^{13}$C-NMR (DMSO-d$^6$, 75 MHz) δ 55.5 (q, Me), 92.6 (d, C5), 98.9 (d, C6), 101.0 (d, C3), 124.7 (d, C7), 114.0 (s, C4a), 134.1 (s, C5a), 144.9 (d, C2), 146.5 (s, C9), 147.7 (s, C10a), 159.1 (s, C4). MS (EI) m/z 216 (M+1, 17), 215 (M$^+$, 100), 214 (M-1, 11), 200 (M-Me, 59), 172 (48). HRMS m/z calculated for C$_{11}$H$_{19}$N$_3$O$_2$: 215.0694; found: 215.0690.

Example 16

8,9-Dihydro-8-methoxymethylpyrido[3',2':4,5]pyrrolo[1,2-c]pyrimidin-9-one (12)

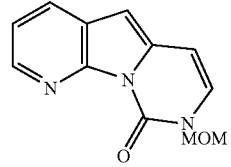

To a cooled (0° C.) solution of 11a (250 mg, 1.4 mmol) in DMF (10 ml), NaH (65 mg, 1.6 mmol) was added. The mixture was stirred for 10 min. and MOMCl (103 µl, 1.4 mmol) was dropwise added. The mixture was stirred at 0° C. for 1 h and quenched with water (1 ml). The solvent was evaporated and the residue dissolved in CH$_2$Cl$_2$. The organic solution was washed with aq. Na$_2$CO$_3$, evaporated and purified by flash column chromatography. Elution with CH$_2$Cl$_2$/MeOH (95/5) gave 12 (267 mg, 87%) as a white solid.

IR (film) ν1711 (s, C=O), 1642 (m, NCO), 1393 (m, C—O), 1175 (m, C—O). $^1$H-NMR (CDCl$_3$, 300 MHz) δ 3.41 (s, 3H, Me), 5.29 (s, 2H, CH$_2$), 6.37 (d, J 7.5, 1H, H6), 6.41 (s, 1H, H5), 7.81 (d, J 7.5, 1H, H7), 7.26 (dd, J 7.8 and 4.8, 1H, H3), 7.90 (dd, J 7.8 and 1.2, 1H, H4), 8.52 (dd, J 4.8 and 1.2, 1H, H2). $^{13}$C-NMR (CDCl$_3$, 50 MHz) δ 56.9 (q, Me), 78.0 (t, CH$_2$), 95.9 (d, C5), 99.6 (d, C6), 119.5 (d, C3), 123.3 (s, C4a), 127.9 (d, C4), 128.1 (d, C7), 135.1 (s, C5a), 143.7 (d, C2), 146.2 (s, C9),147.1 (s, C10a). MS (EI) m/z 230 (M+1, 30), 229 (M$^+$, 100). HRMS m/z calculated for C$_{12}$H$_{11}$N$_3$O$_2$: 229.0851; found: 229.0850.

Example 17

8,9-Dihydro-8-(4-methylphenylsulfonyl)pyrido[3',2': 4,5]pyrrolo[1,2-c]pyrimidin-9-one

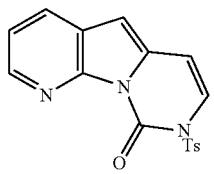

To a cooled (0° C.) solution of 11a (500 mg, 2.7 mmol) in DMF (30 ml), NaH (130 mg, 3.2 mmol) was added. The mixture was stirred for 10 min. and a solution of p-toluen-sulphonyl chloride (570 mg, 3.0 mmol) in DMF (10 ml) was added. The mixture was stirred at room temperature for 1 h. and quenched with water (1 ml). The solvent was evaporated and the residue dissolved in AcOEt. The organic solution was washed with aq. Na$_2$CO$_3$, evaporated and purified by flash column chromatography. Elution with hexane/CH$_2$Cl$_2$ (1/1) gave 8,9-dihydro-8-(4methylphenylsulfonyl)pyrido[3', 2':4,5]-pyrrolo[1,2-c]pyrimidin-9-one (360 mg, 40%) as a white solid.

IR (film) ν1737 (s, C=O), 1642 (m, NCO), 1393 (s, SO$_2$), 1175 (m). $^1$H-NMR (CDCl$_3$, 200 MHz) δ 2.42 (s, 3H, Me), 6.45 (d, J 8.0, 1H, H6), 6.48 (s, 1H, H5), 7.27 (dd, J 8.2 and 4.7, 1H, H3), 7.34 (d, J 8.4, 2H, H3' and H5'), 7.65 (d, J 8.0, 1H, H7), 7.90 (dd, J 8.2 and 1.4, 1H, H4), 8.09 (d, J 8.4, 2H, H2' and H6'), 8.53 (dd, J 4.7 and 1.4, 1H, H2). $^{13}$C-NMR (CDCl$_3$, 50 MHz) δ 21.8 (q, Me), 98.3 (d, C5), 100.2 (d, C6), 118.5 (s, C4'), 120.1 (d, C3), 123.6 (s, C4a), 123.7 (d, C4), 128.6 (d, C7), 129.6 (d, C3' and C5'), 129.8 (d, C2' and C6'), 133.8 (s, C5a), 141.8 (s, C1'), 144.6 (d, C2), 146.0 (s, C9). MS (EI) m/z 340 (M+1, 7), 339 (M$^+$, 32), 184 (M-Ts, 100). HRMS m/z calculated for C$_{17}$H$_{13}$N$_3$O$_3$S: 339.0677; found: 339.0682.

Example 18

8,9-Dihydro-5bromo-8-methoxymethylpyrido[3',2': 4,5]pyrrolo[1,2-c]pyrimidin-9-one (13a)

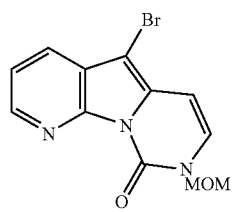

NBS (78 mg, 0.44 mmol) was portionwise added to a solution of 12a (100 mg, 0.44 mmol) in CH$_2$Cl$_2$ (30 ml) at 0° C. and the mixture was stirred for 10 min. The mixture was diluted with CH$_2$Cl$_2$ (50 ml) and washed with saturated aq. NaHCO$_3$ three times. The organic layer was dried and evaporated to obtain 13a (107 mg, 80%) as a light yellow solid without any further purification.

IR (film) ν1715 (s, C=O), 1640 (m, C=C), 1092 (m, C—O). $^1$H-NMR (CDCl$_3$, 300 MHz) δ 3.39 (s, 3H, Me), 5.29 (s, 2H, CH$_2$), 6.43 (d, J 7.8, 1H, H6), 6.90 (d, J 7.8, 1H, H7), 7.33 (dd, J 8.1 and 4.8, 1H, H3), 7.86 (dd, J 8.1 and 1.5, 1H, H4), 8.54 (dd, J 4.8 and 1.5, 1H, H2). $^{13}$C-NMR (CDCl$_3$, 50 MHz) δ 57.0 (q, Me), 77.1 (s, C5), 78.3 (t, CH$_2$), 97.7 (d, C6), 120.1 (d, C3), 122.7 (s, C4a), 126.7 (d, C4), 129.2 (d, C7), 132.8 (s, C5a), 144.8 (d, C2), 146.2 (s, C9), 146.5 (s, C10a). MS (EI) m/z 310 ($^{81}$BrM+1, 5), 309 ($^{81}$BrM$^+$, 50), 308 ($^{79}$BrM+1, 5), 307 ($^{79}$BrM$^+$, 50), 45 (MOM, 100). HRMS m/z calculated for C$_{12}$H$_{10}$$^{79}$BrN$_3$O$_2$: 306.9957; found: 306.9956.

Example 19

8,9-Dihydro-5iodo-8-methoxymethylpyrido[3',2':4, 5]pyrrolo[1,2-c]pyrimidin-9-one (13b)

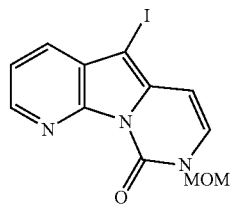

To a cooled (0° C.) solution of 11a (100 mg, 0.44 mmol) in DMF (4 ml) iodine (220 mg, 0.86 mmol) and KOH (94 mg, 1.66 mmol) were simultaneously added. The mixture was stirred for 30 min. at 0° C. The mixture was quenched with an aqueous solution (25 ml) of 0.5% NH$_3$ and 0.1% Na$_2$S$_2$O$_5$. The solution was extracted with AcOEt and the organic solution was washed with saturated aq. NaHCO$_3$ twice. The organic layer was dried and evaporated to obtain 13b (96 mg, 62%) as a light yellow solid without any further purification.

IR (film) ν1714 (s, C=O), 1637 (m, C=C), 1089 (m, C—O). $^1$H-NMR (CDCl$_3$, 300 MHz) δ 3.45 (s, 3H, Me), 5.36 (s, 2H, CH$_2$), 6.46 (d, J 8.1, 1H, H6), 6.99 (d, J 8.1, 1H, H7), 7.40 (dd, J 8.1 and 4.8, 1H, H3), 7.81 (dd, J 8.1 and 1.8, 1H, H4), 8.59 (dd, J 4.8 and 1.8, 1H, H2). $^{13}$C-NMR (CDCl$_3$, 50 MHz) δ 54.5 (s, C5), 57.1 (q, Me), 78.3 (t, CH$_2$), 99.6 (d, C6), 120.3 (d, C3), 125.5 (s, C4a), 128.6 (d, C4), 129.8 (d, C7), 136.5 (s, C5a), 144.9 (d, C2), 146.0 (s, C9), 146.3 (s, C10a). MS (CI, NH$_3$) m/z 357 (M+2, 5), 356 (M+1, 30), 230 (100). HRMS m/z calculated for C$_{12}$H$_{10}$N$_3$O$_2$: 354.9820; found: 354.9823.

Example 20

2-Methanesulfanyl4-trimethylstannylpyrimidine (15)

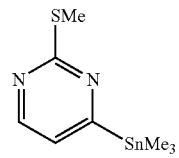

TBAF (5 ml, 1M in THF) was dropwise added to a solution of 4-iodo-2-methalesulfenylpyrimidine (800 mg, 3.2 mmol), hexamethylditin (1 ml, 4.8 mmol), Pd(OAc)$_2$ (45 mg, 0.31 mmol) and PPh$_3$ (90 mg, 0.62 mmol) in THF (10 ml). The mixture was stirred at room temperature for 1.5 hours. The solvent was removed under vacuum and the residue purified by neutral alumina column chromatography. Elution with hexane/AcOEt (99/1) yielded 15 (585 mg, 65%) as a colourless oil.

IR (film) ν1539 (m, C=N), 1402 (m), 1306 (m), 1196 (m). $^1$H-NMR (CDCl$_3$, 300 MHz) δ 0.34 (s, 9H, 3 Me), 2.54 (s, 3H, Me), 7.08 (d, J 4.5, 1H, H5), 8.26 (d, J 4.5, 1H, H6). $^{13}$C-NMR (CDCl$_3$, 75 MHz) δ-9.5 (q, Me), 14.0 (q, Me), 124.5 (d, C5), 153.6 (d, C6), 171.4 (s, C2). MS (EI) m/z 291

($^{120}$SnM$^+$, 50), 276 ($^{120}$SnM-Me, 100). HRMS m/z calculated for C$_8$H$_{14}$N$_2$S$^{120}$Sn: 290.9977; found: 290.9973.

Example 21

8,9-Dihydro5-iodo-8-(4-methylphenylsulphonyl)pyrido[3',2':4,5]pyrrolo[1,2-c]-pyrimidin-9-one (17)

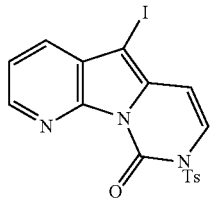

NIS (133 mg, 0.59 mmol) was portionwise added to a cooled (0° C.) solution of 11a (200 mg, 0.59 mmol) in CH$_2$Cl$_2$ (20 ml) and the mixture was stirred for 30 min. at this temperature. The mixture was diluted with CH$_2$Cl$_2$ (50 ml) and washed with water twice. The organic layer was dried and evaporated to obtain 17 (218 mg, 80%) as a light yellow solid without any further purification.

IR (film) v1735 (s, C═O), 1636 (s, NCO), 1395 (m, C—N), 1368 (s, SO$_2$), 1175 (m), 1075 (m). $^1$H-NMR (CDCl$_3$, 300 MHz) δ 2.38 (s, 3H, Me), 6.43 (d, J 8.3, 1H, H6), 7.30 (m, 3H, H3, H3' and H5'), 7.68 (dd, J 8.1 and 1.5, 1H, H4), 7.72 (d, J 8.3, 1H, H7), 8.04 (d, J 8.4, 2H, H2' and H6'), 8.49 (dd, J 4.8 and 1.5, 1H, H2). $^{13}$C-NMR (CDCl$_3$, 75 MHz) δ 21.7 (q, Me), 56.9 (s, C5), 100.0 (d, C6), 120.7 (d, C3), 123.8 (s, C4'), 125.3 (d, C4), 125.7 (s, C4a), 129.0 (d, C7), 129.5 (s, C1'), 129.6 (d, C3' and C5'), 129.7 (d, C2' and C6'), 133.3 (s, C5a), 135.0 (s, C10a), 145.5 (d, C2), 146.1 (s, C9). MS (EI) m/z 466 (M+1, 8), 465 (M$^+$, 36), 310 (M-Ts, 100). HRMS m/z calculated for C$_{17}$H$_{12}$IN$_3$O$_3$S: 464.9646; found: 464.9649.

Example 22

8,9-Dihydro5-(2-methanesulfanylpyrimidin-4-yl)pyrido[3',2':4,5]pyrrolo[1,2-c]-pyrimidin-9-one (18)

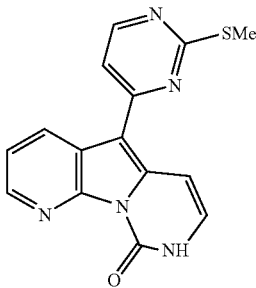

A solution of 17 (50 mg, 0.11 mmol), 2-methanesulfanyl-4-tinethylstannylpyrimidine (93 mg, 0.32 mmol), Pd$_2$(dba)$_3$ (11 mg, 0.011 mmol), PPh$_3$ (6 mg, 0.022 mmol), LiCl (14 mg, 0.32 mmol) and CuI (4 mg, 0.011 mmol) in dioxane (2 ml) was refluxed for 5 h. The solvent was evaporated and the crude was purified by flash column chromatography. Elution with of CH$_2$Cl$_2$/MeOH/aq.NH$_3$ (4/4/2) gave 18 (4 mg, 12%).

$^1$H-NMR (DMSO-d$^6$, 300 MHz) δ 2.60 (3H, s, MeS), 7.20 (1H, d, J 6.3, H7), 7.42 (1H, dd, J 7.5 and 4.2, H3), 7.45 (1H, d, J 5.7, H5'), 7.70 (1H, d, J 6.3, H6), 8.22 (1H, d, J 4.2, H2), 8.39 (1H, d, J 5.7, H6'), 8.73 (1H, d, J 7.5, H4). MS (APCI) AP-m/z 309 (M$^+$, 20), 308 (M-1, 90), 307 (M-2, 100); AP+m/z 331(M+Na, 10), 310 (M+1, 20),309 (M$^+$25).

Example 23

9-Amin pyrid [3',2':4,5]pyrrolo[1,2-c]pyrimidine (19a)

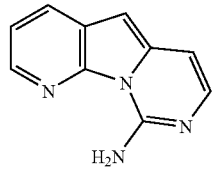

From 11a:

TMSCl (400 μl, 2.70 mmol) was added to a solution of 11a (500 mg, 2.70 mmol) in 2,6-lutidine (40 ml) and HMDSA (60 ml) and the mixture refluxed for 15 h. TMSTf (100 μl, 0.27 mmol) was added and NH$_3$ was bubbled through the mixture for 15 miin. at 0° C. The mixture was closed in a steel bomb reactor and heated at 150° C. for 8 h. (60 psi). The solvent was evaporated and the crude purified by flash column chromatography. Elution with CH$_2$Cl$_2$/MeOH (98/2) gave 19a (150 mg, 30%) as a light yellow solid.

From 23a:

A solution of 23a (20 mg, 0.06 mmol) in liquid NH$_3$ (8 ml) at −78° C. Small portions of Na were added untill blue color was manteined for 10 min. NH$_4$Cl was portionwise added untill blue color desapeared, and the reaction was stirred at room temperature untill solvent was evaporated. The solid residue was disolved in water and extarcted with CH$_2$Cl$_2$. The organic solution was dried and evaporated to obtain 19a (4 mg, 38%) as a yellow solid.

mp 214-215° C.(dec.), (CH$_2$Cl$_2$/hexane). IR (KBr) v3452 (m, NH), 3304 (m, NH), 1654 (m, C═C), 1618 (m, C═C), 1570 (m, C═N), 1403 (m, C—N). $^1$H-NMR DMSO-d$^6$, 300 MHz) δ 6.49 (s, 1H, H5), 6.72 (d, J 6.6, 1H, H6), 6.80 (br, 1H, NH), 7.30 (d, J 6.6, 1H, H7), 7.42 (dd, J 7.8 and 4.6, 1H, H3), 8.14 (dd, J 7.8 and 1.5, 1H, H4), 8.33 (dd, J 4.6 and 1.5, 1H, H2), 8.60 (br, 1H, NH). $^{13}$C-NMR DMSO-d$^6$, 75 MHz) δ 88.8 (d, C5), 101.0 (d, C6), 119.6 (d, C3), 122.9 (s, C4a), 127.5 (d, C4), 136.8 (s, C5a), 138.9 (d, C2), 139.4 (d, C7), 141.8 (s, C10a), 148.8 (s, C9). MS (EI) m/z 185(M+1, 15), 184 (M$^+$, 100), 183 (M−1, 7). HRMS m/z calculated for C$_{10}$H$_8$N$_4$: 184.0749; found: 184.0747.

Example 24

9-Amino4-methoxypyrido[3',2':4,5]pyrrolo[1,2-c]pyrimidine (19b)

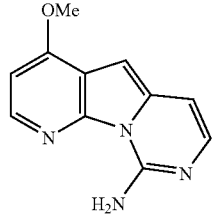

From 11b:

Following the same procedure for 19a, from 11b (60 mg, 0.27 mmol), HMDSA (30 ml), 2,6-lutidine (15 ml) and TMSCl (36 μl, 0.27 mmol). Reaction time 15 h. TMSTf (12 μl, 0.06 mmol) was added and NH$_3$ was bubbled through the mixture for 15 min. at 0° C. Reaction time in a steel bomb reactor 8 h. heated at 150° C. (60 psi). The solvent was evaporated and the crude purified by flash column chromatography. Elution with CH$_2$Cl$_2$/MeOH (99/1) gave 19b (13 mg, 22%) and elution with CH$_2$Cl$_2$/MeOH (95/5) gave 11b (9 mg, 15%).

From 23b:

To a solution of 23b (200 mg, 0.54 mmol) in THF (25 ml) at 0° C. was dropwise added a previously prepared green solution of Na/naphthalene in THF (1.43 ml, 0.54 mmol). After 20 min. The solution was stirred at room temperature and Na/naphthalene in THF (7.2 ml, 2.70 mmol) was dropwise added and the mixture was stirred for 15 min. The solvent was removed and the crude disolved in AcOEt. The organic solution was extracted three times with 4N HCl. The aqueous layers were basified together with NaHCO$_3$ and extracted with CH$_2$Cl$_2$. The organic solution was dried and evaporated and the residue was purified by flash column chromatography. Elution with CH$_2$Cl$_2$/MeOH (95/5) gave 19b (27 mg, 23%) as a light yellow solid.

$^1$H-NMR (CDCl$_3$+CD$_3$OD, 300 MHz) δ 4.01 (s, 3H, Me), 6.45 (s, 1H, H5), 6.61 (d, J 6.6, 1H, H6), 6.75 (d, J 5.6, 1H, H3), 7.14 (d, J 6.6, 1H, H7), 8.18 (d, J 5.6, 1H, H2). $^{13}$C-RMN (CDCl$_3$+CD$_3$OD, 75 MHz) δ 55.6 (q, Me), 87.5 (d, C5), 100.6 (d, C6), 102.2 (d, C3), 114.3 (s, C4a), 134.4 (s, C5a), 136.0 (d, C2), 141.7 (d, C7), 142.8 (s, C10a), 149.0 (s, C9), 158.8 (s, C4). MS (EI) m/z 215 (M+1, 7), 214 (M$^+$, 36), 213 (M−1, 6), 199 (M-Me, 36), 57 (100). (ES+) m/z 216 (M+2, 20), 215 (M+1, 100).

Example 25

9-Acetylaminopyrido[3',2':4,5]pyrrolo[1,2-c]pyrimidine

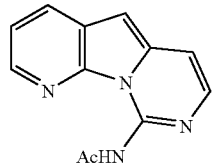

Acetic anhydride (200 μl, 2.04 mmol) was added to a solution of 19a (250 mg, 1.36 mmol) in THF (20 ml) and the mixture was stirred at room temperature for 20 h. The solvent was removed and taken up in CH$_2$Cl$_2$. The solution was washed with saturated aq. NaHCO$_3$. The organic layer was dried and evaporated. The crude was purified by flash column chromatography. Elution with CH$_2$Cl$_2$/MeOH (99/1) gave 9-acetylaminopyrido[3',2':4,5]-pyrrolo[1,2]pyrimidine (225 mg, 75%) as a bright yellow solid.

mp 160-161° C., (CH$_2$Cl$_2$/hexane). IR (KBr) ν3150 (m, NH), 1708 (s, C=O), 1626 (m, NCO), 1574 (m, C=N), 1372 (m, C—N), 1269 (m). $^1$H-NMR (CDCl$_3$, 300 MHz) δ 2.63 (s, 3H, Me), 6.53 (s, 1H, H5), 6.97 (d, J 6.6, 1H, H6), 7.41 (dd, J 8.0 and 4.8, 1H, H3), 7.51 (d, J 6.6, 1H, H7), 8.10 (dd, J 8.0 and 1.5, 1H, H4), 8.41 (dd, J 4.8 and 1.5, 1H, H2). $^{13}$C-NMR (CDCl$_3$, 75 MHz) δ 26.2 (q, Me), 90.5 (d, C5), 107.2 (d, C6), 119.6 (d, C3), 122.8 (s, C4a), 128.4 (d, C4), 136.0 (s, C5a), 136.5 (d, C2), 139.6 (d, C7), 141.3 (s, C10a), 142.3 (s, C9), 170.0 (s, CO). MS (EI) m/z 227 (M+1, 3), 226 (M$^+$, 18), 184 (M-Ac, 100). HRMS m/z calculated for C$_{12}$H$_{10}$N$_4$O: 226.0855; found: 226.0852. Analysis calculated for C$_{12}$H$_{10}$N$_4$O: C (63.71), H (4.46), N (24.77); found: C (63.65), H (4.59), N (24.80).

Example 26

9-Acetylamino4-methoxypyrido[3',2':4,5]pyrrolo[1,2-c]pyrimidine

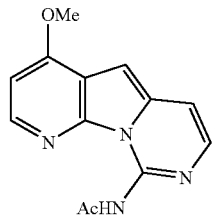

Acetic anhydride (10 μl, 0.05 mmol) was added to a solution of 19b (16 mg, 0.08 mmol) in THF (2 ml) and the mixture was stirred at room temperature for 20 h. The solvent was removed and taken up in CH$_2$Cl$_2$. The solution was washed with saturated aq. NaHCO$_3$. The organic layer was dried and evaporated. 9-Acetylamino-4-methoxypyrido-[3',2':4,5]pyrrolo[1,2-c]pyrimidine (17 mg, 95%) was obtained without any further purification.

$^1$H-NMR (CDCl$_3$, 300 MHz) δ 2.60 (s, 3H, Me), 4.07 (s, 3H, Me), 6.60 (s, 1H, H5), 6.82 (d, J 5.7, 1H, H3), 6.96 (d, J 6.6, 1H, H6), 7.47 (d, J 6.6, 1H, H7), 8.29 (d, J 5.7, 1H, H2). $^{13}$C-NMR (CDCl$_3$, 75 MHz) δ 26.3 (q, Me), 55.8 (q, Me), 88.1 (d, C5), 100.7 (d, C6), 107.7 (d, C3), 114.1 (s, C4a), 134.5 (s, C5a), 135.9 (d, C2), 142.1 (d, C7), 159.5 (s, C4), 170.1 (s, CO). MS (ES+) m/z 258 (M+2, 30), 257 (M+1, 100).

Example 27

9-Acetylamino-5-iodopyrido[3',2':4,5]pyrrolo[1,2-c]pyrimidine (20a)

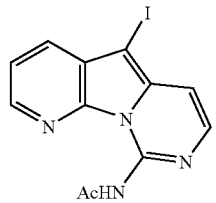

NIS (100 mg, 0.44 mmol) was portionwise added to a cooled (0° C.) solution of 9-Acetylaminopyrido[3',2':4,5]pyrrolo[1,2-c]pyrimidine (100 mg, 0.44 mmol) in CH$_2$Cl$_2$ (20 ml). The mixture was stirred for 15 min. The solution was diluted with CH$_2$Cl$_2$ (50 ml) and washed twice with water. The organic layer was dried and evaporated to obtain 20a (142 mg, 93%) as a bright yellow solid mp 163-164° C.(dec.), (CH$_2$Cl$_2$/hexane). IR (KBr) ν3050 (m, NH), 1694 (m, C=O), 1573 (m, C=N), 1372 (m, C—N), 1307 (m). $^1$H-NMR (CDCl$_3$, 200 MHz) δ 2.63 (s, 3H, Me), 6.94 (d, J 6.4, 1H, H6), 7.47 (dd, J 8.2 and 4.8, 1H, H3), 7.61 (d, J 6.4, 1H, H7), 7.93 (dd, J 8.2 and 1.6, 1H, H4), 8.40 (dd, J 4.8 and 1.6, 1H, H2). $^{13}$C-NMR (CDCl$_3$, 75 MHz) δ 26.4 (q, Me), 46.7 (s, C5), 107.0 (d, C6), 120.6 (d, C3), 125.2 (s, C4a), 128.8 (d, C4), 136.9 (s, C5a), 138.6 (d, C7), 140.9 (d, C2), 141.5 (s, C10a), 142.7 (s, C9), 170.2 (s, CO). MS (EI) m/z 353 (M+1, 3), 352 (M$^+$, 22), 310 (M-Ac, 100). HRMS m/z calculated for C$_{12}$H$_9$IN$_4$O: 351.9821; found: 351.9821. Analysis calculated for C$_{12}$H$_9$IN$_4$O: C (40.93), H (2.58), N (15.91); found: C (40.91), H (2.64), N (15.79).

Example 28

9-Acetylamino-5-iodo-4-methoxypyrido[3',2':4,5]pyrrolo[1,2-c]pyrimidine (20b)

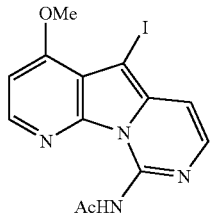

NIS (18 mg, 0.078 mmol) was portionwise added to a cooled (0° C.) solution of 9-Acetylamino-4-methoxypyrido[3',2':4,5]pyrrolo[1,2-c]pyrimidine (20 mg, 0.078 mmol) in $CH_2Cl_2$ (15 ml). The mixture was stirred for 15 min. The solution was diluted with $CH_2Cl_2$ (50 ml) and washed twice with water. The organic layer was dried and evaporated to obtain 20b (27 mg, 93%).

$^1$H-NMR (CDCl$_3$, 200 MHz) δ 2.61 (s, 3H, Me), 4.08 (s, 3H, Me), 6.84 (d, J 5.7, 1H, H3), 6.97 (d, J 6.6, 1H, H6), 7.57 (d, J 6.6, 1H, H7), 8.31 (d, J 5.7, 1H, H2). $^{13}$C-NMR (CDCl$_3$, 75 MHz) δ 26.3 (q, Me), 55.8 (q, Me), 101.2 (d, C6), 107.7 (d, C3), 114.1 (s, C4a), 133.5 (s, C5a), 137.7 (d, C2), 142.5 (d, C7), 142.6 (s, C10a), 151.8 (s, C9), 170.4 (s, C4), 176.8 (s, CO). MS (ES+) m/z 384 (M+2, 15), 383 (M+1, 100), 192 (M+2$^{2+}$, 50), 191 (M+1$^{2+}$, 22).

Example 29

9-Amino-5-(2-methanesulfanylpyrimidin-4-yl)pyrido[3',2':4,5]pyrrolo[1,2-c]pyrimidine (21) and 9-Acetylamino-5-(2-methanesulfanylpyrimidin-4-yl)pyrido[3',2':4,5]-pyrrolo-[1,2-c]pyrimidine

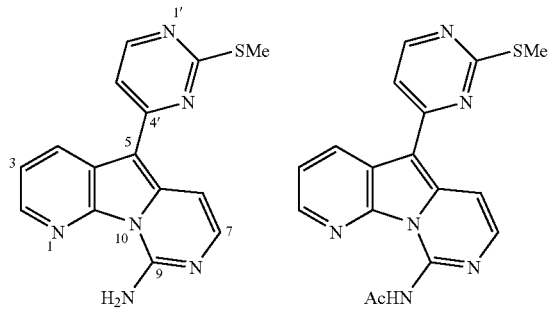

A solution of 20a (130 mg, 0.37 mmol), 2-methanesulfenyl-4-trimethylstannylpyrimidine (93 mg, 1.10 mmol), Pd$_2$(dba)$_3$ (76 mg, 0.07 mmol), PPh$_3$ (39 mg, 0.15 mmol), LiCl (47 mg, 1.10 mmol) and CuI (14 mg, 0.07 mmol) in dioxane (10 ml) was refluxed for 1.5 hours. The organic solvent was removed and the oil dissolved in $CH_2Cl_2$. The organic solution was extracted four times with 4N HCl and the aqueous solution basified with solid $Na_2CO_3$. The aqueous solution was extracted with $CH_2Cl_2$. The organic layer was evaporated and purified by flash column chromatography. Elution with $CH_2Cl_2$/MeOH (99/1) gave 9-Acetylamino-5-(2-methanesulfenylpyrimidin-4-yl)pyrido[3',2':4,5]pyrrolo[1,2-c]pyrimidine (21 mg, 16%) as a yellow solid and with $CH_2Cl_2$/MeOH (95/5) gave 21 (30 mg, 26%) as a yellow solid.

A solution of 9-acetylamino-5-(2-methanesulfenylpyrimidin-4-yl)pyrido[3',2':4,5]-pyrrolo[1,2-c]pyrimidine (15 mg, 0.043 mmol) in 5N HCl/MeOH (5 ml) was refluxed for 1 hour. The solvent was removed and the residue dissolved in saturated aq. $Na_2CO_3$. The solution was extracted with $CH_2Cl_2$. The organic solvent was evaporated. 21 (12 mg, 90%) was obtained.

When the reaction was repeated and the HCl/MeOH treatment was done just before the purification by flash column chromatography 21 (45%) was obtained as only product.

9-Amino-5-(2-methanesulfenylpyrimidin-4-yl)pyrido[3',2':4,5]pyrrolo[1,2-c]pyrimidine (21)

mp 223-224° C. ($CH_2Cl_2$/hexane). IR (KBr) ν3390 (m, NH), 1632 (m, C=C), 1557 (m, C=N), 1517 (m), 1464 (m, C—N), 1265 (m). $^1$H-NMR (CDCl$_3$, 300 MHz) δ 2.68 (s, 3H, Me), 7.33 (d, J 5.4, 1H, H5'), 7.49 (dd, J 8.4 and 4.8, 1H, H3), 7.58 (d, J 6.6, 1H, H7), 7.68 (d, J 6.6, 1H, H6), 8.40 (dd, J 4.8 and 1.6, 1H, H2), 8.48 (d, J 5.4, 1H, H6'), 8.73 (dd, J 8.4 and 1.6, 1H, H4). $^{13}$C-NMR (CDCl$_3$, 50 MHz) δ 14.4 (q, MeS), 100.3 (s, C5), 102.1 (d, C6), 112.6 (d, C5'), 120.7 (d, C3), 122.0 (s, C4a), 128.6 (d, C4), 138.7 (s, C5a), 140.3 (d, C2), 142.1 (s, C10a), 143.4 (d, C7), 149.8 (s, C9), 156.5 (d, C6'), 161.2 (s, C4'), 172.3 (s, C2'). MS (EI) m/z 309 (M+1, 7), 308 (M$^+$, 33). HRMS m/z calculated for $C_{15}H_{12}N_6S$: 308.0844; found: 308.0839. UV (MeOH) λ217 (16,324), 252 (21,415), 400 (11,692).

9-Acetylamino-5-(2-methanesulfenylpyrimidin-4-yl)pyrido[3',2':4,5]pyrrolo[1,2-c]pyrimidine mp 160-162° C. ($CH_2Cl_2$/hexane). IR (KBr) ν1704 (s, C=O), 1620 (m, C=C), 1556 (m), 1536 (m, C=N), 1517 (m), 1502 (m), 1476 (m, C—N), 1265 (m). $^1$H-NMR (CDCl$_3$, 200 MHz) δ 2.67 (s, 3H, Me), 2.69 (s, 3H, MeS), 7.36 (d, J 5.2, 1H, H5'), 7.58 (dd, J 8.2 and 4.8, 1H, H3), 7.83 (d, J 6.6, 1H, H7), 7.93 (d, J 6.6, 1H, H6), 8.52 (dd, J 4.8 and 1.4, 1H, H2), 8.54 (d, J 5.2, 1H, H6'), 8.77 (dd, J 8.2 and 1.4, 1H, H4). $^{13}$C-NMR (CDCl$_3$, 75 MHz) δ 14.4 (q, MeS), 26.4 (q, Me), 104.5 (s, C5), 107.4 (d, C6), 113.0 (d, C5'), 121.1 (d, C3), 121.6 (s, C4a), 129.5 (d, C4), 137.7 (s, C5a), 141.0 (d, C2), 141.1 (d, C7), 142.5 (s, C10a), 143.3 (s, C9), 156.8 (d, C6'), 160.7 (s, C4'), 170.2 (s, C2'), 172.7 (s, CO). MS (EI) m/z 351 (M+1, 3), 350 (M$^+$, 33), 308 (M-Ac, 100). HRMS m/z calculated for $C_{17}H_{14}N_6OS$: 350.0949; found: 350.0940. UV (MeOH) λ255 (25,480), 400 (17,710).

Example 30

9-Amino-5-(2-methanesulfinylpyrimidin-4-yl)pyrido[3',2':4,5]pyrrolo[1,2-c]pyrimidine

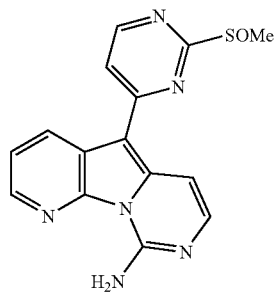

To a cooled (0° C.) solution of 21 (20 mg, 0.07 mmol) in $CH_2Cl_2$ (5 ml) mCPBA (32 mg, 0.13 mmol) was added. The mixture was stirred for 30 min. A saturated aq. $Na_2S_2O_3$ solution was added (1 ml) and was basified with saturated aq. Na₂CO₃. The organic layer was separated and the aqueous layer extracted with CH₂Cl₂. The organic solutions were dried and evaporated together to give 9-amino-5-(2-methanesulfinylpyrimidin-4-yl)pyrido[3',2':4,5]-pyrrolo[1,2-c]pyrimidine (20 mg, 90%).

IR (film) v3388 (m, NH), 1635 (m, C=C), 1569 (m), 1519 (m, C=N), 1467 (m), 1267 (s, S=O). ¹H-NMR (CDCl₃, 200 MHz) δ 3.03 (s, 3H, Me), 7.53 (dd, J 8.2 and 4.8, 1H, H3), 7.63-7.78 (m, 3H, H7, H6 and H5'), 8.42 (dd, J 4.8 and 1.4, 1H, H2), 8.73 (d, J 5.4, 1H, H6'), 8.84 (dd, J 8.2 and 1.4, 1H, H4). ¹³C-NMR (CDCl₃, 50 MHz) δ 40.3 (q, Me), 99.5 (s, C5), 102.2 (d, C6), 116.5 (d, C5'), 121.3 (d, C3), 121.9 (s, C4a), 129.1 (d, C4), 140.0 (s, C5a), 140.8 (d, C2), 143.8 (s, C10a), 144.6 (d, C7), 150.0 (s, C9), 157.3 (d, C6'), 162.6 (s, C4'), 163.5 (s, C2'). MS (EI) m/z 324 (M⁺, 47), 261 (M-SOMe, 100); (ES+) m/z 326 (M+2, 20), 325 (M+1, 100).

Example 31

9-Amino5-(2-methanesulfonylpyrimidin-4-yl)pyrido[3',2':4,5]pyrrolo[1,2-c]pyrimidine

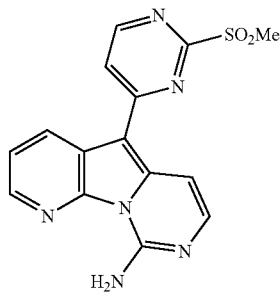

Method A

To a solution of 9-Amino-5-(2-methanesulfinylpyrimidin-4-yl)-pyrido[3',2':4,5]-pyrrolo[1,2-c]pyrimidine (50 mg, 0.16 mmol) in CH₂Cl₂ (15 ml) mCPBA (88 mg, 0.36 mmol) was added at room temperature. The mixture was stirred for 2 h. A saturated aq. Na₂S₂O₃ solution was added (1 ml) and was basified with saturated aq. Na₂CO₃. The organic layer was separated and the aqueous layer extracted with CH₂Cl₂. The organic solutions were evaporated together and 9-Amino-5-(2-methanesulfonylpyrimidin-4-yl)pyrido[3',2':4,5]-pyrrolo[1,2-c]pyrimidine (50 mg, 91%) as a light orange solid was obtained.

Method B

To solution of 21 (200 mg, 0.65 mmol) in CH₂Cl₂ (50 ml) mCPBA (320 mg, 1.30 mmol) was added. The mixture was stirred for 2 hours at room temperature. A saturated aq. Na₂S₂O₃ solution was added (5 ml) and was basified with saturated aq. Na₂CO₃. The organic layer was separated and the aqueous layer extracted with CH₂Cl₂. The organic solutions were dried and evaporated together to give 9-Amino-5-(2-methanesulfonylpyrimidin-4-yl)pyrido[3',2':4,5]-pyrrolo[1,2-c]pyrimidine(201 mg, 91%).

mp 118-189° C. (CH₂Cl₂/hexane). IR (film) v3340 (m, NH), 1569 (m, C=C), 1517 (m), 1462 (m), 1262 (s, SO₂). ¹H-NMR (CDCl₃, 300 MHz) δ 3.41 (s, 3H, Me), 7.56 (dd, J 8.1 and 4.8, 1H, H3), 7.69 (d, J 6.6, 1H, H7), 7.78 (d, J 5.7, 1H, H5'), 7.80 (d, J 6.6, 1H, H6), 8.44 (dd, J 4.8 and 1.5, 1H, H2), 8.75 (d, J 5.7, 1H, H6'), 8.84 (dd, J 8.1 and 1.5, 1H, H4). ¹³C-NMR (DMSO-d⁶, 50 MHz) δ 39.8 (q, Me), 97.4 (s, C5), 101.0 (d, C6), 118.4 (d, C5'), 121.0 (s, C4a), 121.2 (d, C3), 128.6 (d, C4), 130.3 (s, C5a), 140.5 (d, C2), 143.3 (s, C10a), 146.8 (d, C7), 149.9 (s, C9), 157.5 (d, C6'), 161.5 (s, C4'), 165.2 (s, C2'). MS (CI, NH₃) m/z 342 (M+2, 6), 341 (M+1, 20), 340 (M⁺, 100), 309 (M-O₂, 5), 263 (M-SO₂Me, 25). HRMS m/z calculated for C₁₅H₁₂N₃O₂S: 340.0742; found: 340.0740.

Example 32

9-Amino-5-(2-aminopyrimidin-4-yl)pyrido[3',2':4,5]pyrrolo[1,2-c]-pyrimidine (5a)

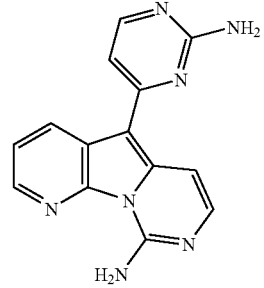

Method A

A solution of 9-Amino-5-(2-methanesulfonylpyrimidin-4-yl)pyrido-[3',2':4,5]pyrrolo[1,2-c]pyrimidine (25 mg, 0.04 mmol) in dioxane (3 ml) and 23% aq. NH₃ (5 ml) was heated in a sealed tube at 80° C. for 6 h. The mixture was cooled and the solvent removed. The residue was dissolved in saturated aq. Na₂CO₃ and extracted with CH₂Cl₂ several times. The organic layers were dried and evaporated. The crude was purified by flash column chromatography. Elution with CH₂Cl₂/MeOH (97/3) gave 5a (18 mg, 90%) as a yellow solid.

Method B

A solution of 20a (120 mg, 0.36 mmol), 27 (200 mg, 0.72 mmol), Pd₂(dba)₃ (75 mg, 0.06 mmol), PPh₃ (35 mg, 0.14 mmol), LiCl (42 mg, 1.10 mmol) and CuI (12 mg, 0.06 mmol) in dioxane (4ml) was refluxed for 1.5 hours. The organic solvent was removed and the oil dissolved and refluxed in HCl/MeOH for 1 h. The solvent was evaporated and dissolved in CH₂Cl₂. The organic solution was extracted with 4N HCl four times and the aqueous solution basified with solid Na₂CO₃. The aqueous solution was extracted with CH₂Cl₂. After evaporation of the solvent the mixture was purified by flash column chromatography. Elution with CH₂Cl₂/MeOH (95/5) 5a (50 mg, 54%) as a yellow solid was obtained.

mp 160-162° C. (CH₂Cl₂/hexane). IR (film) v3332 (m, NH), 1632 (m, C=C), 1574 (m, C=N), 1454 (m, C—N), 1262 (m). ¹H-NMR (DMSO-d⁶, 500 MHz) δ 6.63 (br, 2H, 2'NH₂), 7.12 (d, J 5.5, 1H, H5'), 7.64 (d, J 8.0 and 4.4, 1H, H3), 7.70 (d, J 6.6, 1H, H7), 7.76 (d, J 6.6, 1H, H6), 8.29 (d, J 5.5, 1H, H6'), 8.51 (dd, J 4.4 and 1.4, 1H, H2), 8.52 (br, 1H, 9NH), 8.99 (dd, J 8.0 and 1.4, 1H, H4), 9.35 (br, 1H, 9NH). ¹³C-NMR (DMSO-d⁶, 50 MHz) δ 99.5 (s, C5), 101.7 (d, C6), 106.8 (d, C5'), 120.7 (d, C3), 121.6 (s, C4a), 129.1 (d, C4), 138.2 (s, C5a), 140.1 (d, C2), 142.8 (s, C10a), 143.8 (d, C7), 149.7 (s, C9), 158.0 (d, C6'), 161.4 (s, C4'), 163.5 (s, C2').

MS (ES+) m/z 279 (M+2, 20), 278 (M+1, 100), 277 (M⁺, 10). HRMS m/z calculated for C₁₅H₁₁N₇: 277.1075; found: 277.1071. UV (MeOH) 225 (36,010), 250 (34,126), 350(20,942), 400 (26,481).

Example 33

9-Amino-5-(2-aminopyrimidin-4-yl)pyrido[3',2':4,5]pyrrolo[1,2-c]-pyrimidine (5b)

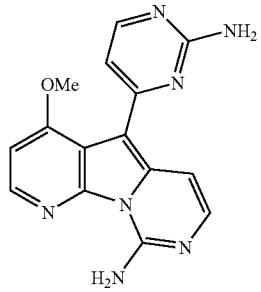

Following the same procedure for 5a (Method B). From 20b (26 mg, 0.07 mmol), 27 (32 mg, 0.11 mmol), Pd$_2$(dba)$_3$ (15 mg, 0.014 mmol), PPh$_3$ (7 mg, 0.028 mmol), LiCl (9 mg, 0.21 mmol) and CuI (3 mg, 0.014 mmol) in dioxane (3 ml), refluxed for 1 h After purification by flash column chromatography 5b (8 mg, 38%) was obtained.

$^1$H-NMR (CDCl$_3$, 200 MHz) δ 4.03 (s, 3H, Me), 6.90 (d, J 5.4, 1H, H3), 7.08 (d, J 5.4, 1H, H6), 7.50 (d, J 5.4, 1H, H7), 7.54 (d, J 5.0, 1H, H5'), 8.28 (d, J 5.4, 1H, H2), 8.47 (d, J 5.0, 1H, H6') MS (ES+) m/z 308 (M+1, 100), 307 (M$^+$, 20).

Example 34

9-Tosylamino-4-tetrahydropyranoxypyrido[3',2':4,5]pyrrolo[1,2-c]pyrimidine (22a)

A soluction of 9a (235 mg, 0.88 mmol) and DIPEA (505 μl, 1.98 mmol) in CH$_2$Cl$_2$ (20 ml) was slowly added to a solution of TsNCCl$_2$ (250 mg, 0.99 mmol) in CH$_2$Cl$_2$ (20 ml). The solution was stirred for 30 min and washed with water. The organic solution was dried, filtered and evaporated to give a crude which was purificated by flash column chromatography. Elution with DCM/MeOH (99/1) gave 22a (235 mg, 60%) as a light orange solid.

IR (film) ν3312 (m, NH), 1639 (s, N=C), 1472 (m, C—N), 1277 (m, C—O). $^1$H-NMR (CDCl$_3$, 200 MHz) δ 1.40-1.80 (m, 6H, H3', H4' and H5'), 2.38 (s, 3H, Me), 3.45-4.00 (m, 4H, H7 and H6'), 4.65 and 4.95 (bt, 1H, H2'), 5.02 and 5.05 (bt, 1H, H6), 6.59 and 6.61 (s, 1H, H5), 7.20 and 7.21 (dd, J 7.8 and 4.8, 1H, H3), 7.27 (d, J 8.4, 2H, Ts), 7.84 and 7.85 (dd, J 7.8 and 1.5, 1H, H4), 8.12 (d, J 8.4, 2H, Ts), 8.40 (br, 1H, NH), 8.50 and 8.52 (dd, J 4.8 and 1.5, 1H, H2). $^{13}$C-NMR (CDCl$_3$, 50 MHz) δ 18.7 and 19.1 (t, C4'), 21.5 (q, Ts), 25.2 and 25.3 (t, C5'), 29.9 and 30.3 (t, C3'), 43.1 and 44.7 (t, C6'), 62.2 and 62.5 (t, C7), 62.6 and 63.8 (d, C6), 95.7 and 96.8 (d, C2'), 104.1 and 105.5 (d, C5), 119.2 (d, C3), 121.5 (s, C4a), 126.4 (d, Ts), 129.2 (d, C4), 131.9 and 134.7 (s, C5a), 140.0 and 142.5 (s, C10a), 145.6 and 145.9 (d, C2), 148.1 (s, C9). MS (EI) m/z 440 (M$^+$, 1), 376 (M-SO$_2$, 19).

Example 35

4-Methoxy-9-tosylamino-6-tetrahydropyranoxypyrido[3',2':4,5]pyrrolo[1,2-c]-pyrimidine (22b)

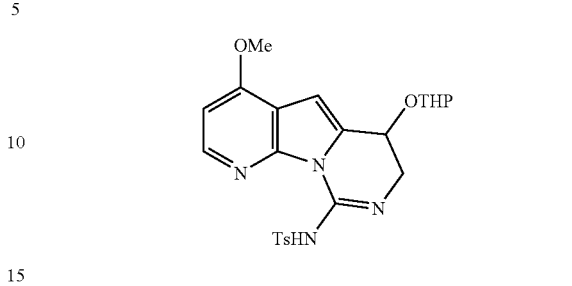

Following the methodology for 22a, from 9b (1 g, 3.44 mmol), DIPEA (1.9 ml, 7.58 mmol) and TsNCCl$_2$ (952 mg, 3.78 mmol) compound 22b (1.05 g, 65%) as a light orange solid was obtained.

$^1$H-NMR (CDCl$_3$, 200 MHz) δ 1.40-1.80 (m, 6H, H3', H4' and H5'), 2.38 (s, 3H, Me), 3.45-3.95 (m, 4H, H7 and H6'), 3.97 (s, 3H, Me), 4.62 and 4.95 (bt, 1H, H2'), 5.01 (m, 1H, H6), 6.69 (m, 1H, H3 and H5), 7.26 (d, J 8.4, 2H, Ts), 8.10 (d, J 8.4, 2H, Ts), 8.41 and 8.42 (d, J 5.8, 1H, H2). $^{13}$C-NMR (CDCl$_3$, 50 MHz) δ 18.5 and 19.3 (t, C4'), 21.6 (q, Ts), 25.2 and 25.3 (t, C5'), 30.0 and 30.2 (t, C3'), 43.3 and 44.9 (t, C6'), 55.6 (q, Me), 61.9 and 62.3 (t, C7), 62.7 and 63.5 (d, C6), 95.5 and 96.4 (d, C2'), 101.3 (d, C3), 101.5 and 102.9 (d, C5), 126.2 (s, C4a), 126.5 (d, Ts), 129.2 (d, Ts), 129.3 and 129.5 (s, C5a), 132.2 (s, Ts), 142.5 (s, C10a), 147.6 and 147.9 (d, C2), 159.7 (s, C9).

Example 36

4-Chloro-9-tosylamino-6-tetrahydropyranoxypyrido[3',2':4,5]pyrrolo[1,2-c]pyrimidine (22c)

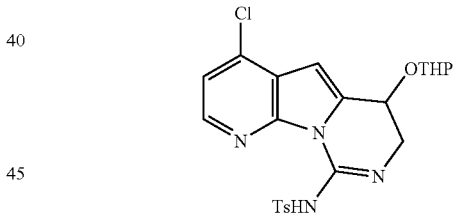

Following the methodology for 22a. From 9c (175 mg, 0.59 mmol), DIPEA (225 μl, 1.30 mmol) and TsNCCl$_2$ (164 mg, 0.65 mmol) compound 22c (165 mg, 60%) was obtained.

IR (film) ν3309 (m, NH), 1634 (s, N=C), 1471 (m, C—N), 1358 (m, SO$_2$), 1280 (m, C—O). $^1$H-NMR (CDCl$_3$, 200 MHz) δ 1.40-1.80 (m, 6H, H3', H4' and H5'), 2.38 (s, 3H, Me), 3.45-3.95 (m, 4H, H7 and H6'), 4.65 and 4.95 (m, 1H, H2'), 5.01 (m, 1H, H6), 6.71 and 6.72 (s, 1H, H5), 7.24 and 7.25 (d, J 5.4, 1H, H3), 7.27 (d, J 8.0, 2H, Ts), 8.10 (d, J 8.4, 2H, Ts), 8.39 and 8.41 (d, J 4.8, 1H, H2) 8.48 (br, 1H, NH). $^{13}$C-NMR (CDCl$_3$, 50 MHz) δ 18.8 and 19.1 (t, C4'), 21.6 (q, Ts), 25.2 and 25.3 (t, C5'), 30.0 and 30.3 (t, C3'), 43.1 and 44.7 (t, C6'), 62.5 and 62.6 (t, C7), 63.3 and 63.6 (d, C6), 95.8 and 96.8 (d, C2'), 101.9 and 103.2 (d, C5), 119.3 (d, C3), 127.3 (s, C4a), 126.4 (d, Ts), 129.2 (d, Ts), 132.2 (s, Ts), 135.5 and 136.4 (s, C5a), 139.8 (s, Ts), 142.6 (s, C10a), 145.8 and 146.2 (d, C2), 147.9 and 148.1 (s, C9). MS (EI) m/z 475 (M$^+$, 1), 410 (M-SO$_2$, 20).

Example 37

9-Tosylamino-6-hydroxypyrido[3',2':4,5]pyrrolo[1,2-c]pyrimidine

A solution of 22a (210 mg, 0.48 mmol) was dissolved in CH$_2$Cl$_2$ (25 mL), 4N HCl aqueous solution (25 mL) was added and the mixture was energically stirred for 20 min. The solution was basified and the organic solution was separated. The aqueuos layer was extracted twice with CH$_2$Cl$_2$. The organic solutions were evaporated together and purified by flash column chromatography. Elution with CH$_2$Cl$_2$/MeOH (95/5) gave 9-tosylamino-6-hydroxypyrido[3',2':4,5]pyrrolo[1,2-c]pyrimidine (160 mg, 95%) as a pale yellow solid.

IR (film) ν3315 (m, NH), 1624 (s, C=N), 1473 (s, N—C), 1276 (m, SO$_2$), 1135 (m, C—O). $^1$H-NMR (CDCl$_3$, 300 MHz) δ 2.35 (s, 3H, Me), 3.50 (m, 1H, H7), 3.75 (m, 1H, H7), 5.04 (br, 1H, H6), 6.55 (s, 1H, H5), 7.00 (dd, J 7.8 and 4.8, 1H, H3), 7.24 (d, J 8.4, 2H, Ts), 7.71 (dd, J 7.8 and 1.5, 1H, H4), 8.03 (d, J 8.4, 2H, Ts), 8.27 (dd, J 4.8 and 1.5, 1H, H2), 8.42 (br, 1H, NH). $^{13}$C-NMR (CDCl$_3$, 75 MHz) δ 21.5 (q, Me), 45.8 (t, C7), 60.4 (d, C6), 101.7 (d, C5), 103.7 (d, C3), 119.1 (d, C4), 122.2 (s, C4a), 126.5 (d, Ts), 129.2 (d, Ts), 129.4 (d, C4), 136.7 (s, C5a), 139.6 (s, Ts), 142.7 (s, C10a), 144.9 (d, C2), 147.5 (s, Ts), 148.5 (s, C9). MS (EI) m/z 357 (M+1, 1), 356 (M$^+$, 3), 338 (M-H$_2$O, 2), 292 (M-SO$_2$, 18).

Example 38

4-Methoxy-9-tosylamino-6-hydroxypyrido[3',2':4,5]pyrrolo[1,2-c]pyrimidine

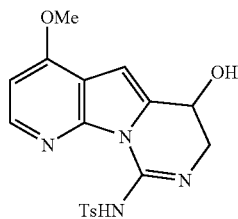

Following the methodology for previous compound, from 22b (1.05 g, 2.23 mmol) compound 4-methoxy-9-tosylamino-6-hydroxypyrido-[3',2':4,5]pyrrolo [1,2-c]pyrimidine (819 mg, 95%) was obtained as a light yellow solid.

IR (film) ν3317 (m, NH), 1627 (s, C=N), 1475 (s, N—C), 1293 (m, SO$_2$), 1139 (m, C—O). $^1$H-NMR (CDCl$_3$, 200 MHz) δ 2.5 (s, 3H, Me), 3.50 (m, 1H, H7), 3.75 (m, 1H, H7), 3.85 (s, 3H, Me), 5.02 (br, 1H, H6), 6.43 (d, J 5.4, 1H, H3), 6.52 (s, 1H, H5), 7.24 (d, J 8.0, 2H, Ts), 8.04 (d, J 8.0, 2H, Ts), 8.09 (d, J 5.4, 1H, H2), 8.41 (br, 1H, NH). $^{13}$C-NMR (CDCl$_3$, 50 MHz) δ 21.5 (q, Me), 45.9 (t, C7), 55.6 (q, Me), 60.1 (d, C6), 100.8 (d, C3), 101.4 (d, C5), 112.1 (s, C4a), 126.5 (d, Ts), 129.3 (d, Ts), 134.3 (s, C5a), 139.6 (s, Ts), 142.7 (s, C10a), 146.7 (d, C2), 148.6 (s, C9), 159.6 (s, C4).

Example 39

4-Chloro-9-Tosylaminio6-hydroxypyrido[3',2':4,5]pyrrolo[1,2-c]poyrimidine

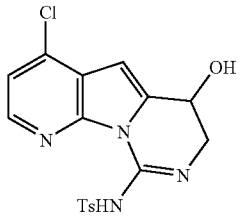

Following the methodology for previous compound, from 22c (50 mg, 0.11 mmol) compound 4-chloro-9-tosylamino-6-hydroxypyrido-[3',2':4,5]pyrrolo[1,2-c]pyrimidine (37 mg, 90%) was obtained.

IR (film) ν3316 (m, NH), 1632 (s, C=N), 1472 (s, N—C), 1277 (m, SO$_2$), 1082 (m, C—O). $^1$H-NMR (CDCl$_3$, 200 MHz) δ 2.35 (s, 3H, Me), 3.56 (brd, J 13.6, 1H, H7), 3.80 (dt, J 13.6 and 2.6, 1H, H7), 4.80 (br, 1H, OH), 5.10 (br, 1H, H6), 6.61 (s, 1H, H5), 7.04 (d, J 5.0, 1H, H3), 7.24 (d, J 8.2, 2H, Ts), 8.03 (d, J 8.2, 2H, Ts), 8.16 (d, J 5.0, 1H, H2), 8.46 (br, 1H, NH). $^{13}$C-NMR (CDCl$_3$, 50 MHz) S 21.6 (q, Me), 45.7 (t, C7), 60.4 (d, C6), 101.5 (d, C5), 119.2 (d, C3), 121.4 (s, C4a), 126.5 (d, Ts), 129.3 (d, Ts), 131.0 (s, Ts), 136.5 (s, C5a), 137.4 (s, Ts), 142.8 (s, C10a), 145.2 (d, C2), 148.3 (s, C9). MS (EI) m/z 392 ($^{37}$ClM$^+$, 2), 390 ($^{35}$ClM$^+$, 6), 328 ($^{37}$ClM-SO$_2$, 10), 326 ($^{35}$ClM-SO$_2$, 31). HRMS m/z calculated for C$_{17}$H$_{15}$ClN$_4$O$_5$S: 390.0553; found: 390.0548.

Example 40

9-Tosylaminopyrido[3',2':4,5]pyrrolo[1,2-c]pyrimidine (23a)

A solution of 9-tosylamino-6-hydroxypyrido[3',2':4,5]pyrrolo[1,2-c]pyrimidine (170 mg, 0.48 mmol) and TEA (133 μl, 0.96 mmol) was dissolved in CH$_2$Cl$_2$ (25 ml), methanesulfonylchloride (37 μl, 0.48 mmol) was dropwise added and the mixture was stirred for 20 min. The solution was washed with water and the organic solutions was dried and evaporated. The crude mixture was purified by flash column chromatography. Elution with CH$_2$Cl$_2$/MeOH (98/2) gave 23a (124 mg, 78%) as a yellow solid.

IR (KBr) ν3266 (m, NH), 1604 (s, C=N), 1399, 1281 (m, SO$_2$). $^1$H-NRM (CD$_3$OD, 300 MHz) δ 2.35 (s, 3H, Me), 6.69 (s, 1H, H5), 6.73 (d, J 7.8, 1H, H6), 7.04 (d, J 7.8, 1H, H7), 7.31 (d, J 8.4, 2H, Ts), 7.44 (dd, J 8.1 and 5.1, 1H, H3), 7.99 (d, J 8.4, 2H, Ts), 8.15 (d, J 8.1, 1H, H4), 8.46 (d, J 5.1, 1H, H2). MS (EI) m/z 339 (M+1, 4), 338 (M$^+$, 19), 273 (M-SO$_2$, 100). HRMS m/z calculated for C$_{17}$H$_{14}$N$_4$O$_2$S: 338.0837; found: 338.0841.

Example 41

4-Methoxy-9-tosylaminopyrido[3',2':4,5]pyrrolo[1,2-c]pyrimidine (23b)

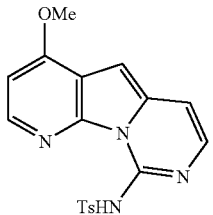

Following the methodology for 23a, from 4-methoxy-9-tosylamino-6-hydroxypyrido[3',2':4,5]pyrrolo[1,2-c]pyrimidine (170 mg, 0.48 mmol) compound 23b (124 mg, 78%) was obtained as a light yellow solid.

IR (KBr) ν3266 (m, NH), 1604 (s, C=N), 1399, 1293 (m, SO$_2$), 1141. $^1$H-NMR (CD$_3$OD, 300 MHz) δ 2.35 (s, 3H, Me), 4.01 (s, 3H, Me), 6.57 (s, 1H, H5), 6.64 (d, J 7.5, 1H, H6), 6.93 (d, J 6.0, 1H, H3), 6.98 (d, J 7.5, 1H, H7), 7.30 (d, J 8.1, 2H, Ts), 8.00 (d, J 8.1, 2H, Ts), 8.30 (d, J 6.0, 1H, H2). $^{13}$C-NMR (DMSO-d$^6$, 50 MHz) δ 21.0 (q, Me), 55.9 (q, Me), 93.0 (d, C5), 101.5 (d, C6), 102.1 (d, C3), 113.9 (s, C4a), 125.9 (d, Ts), 129.3 (d, C2 and Ts), 132.6 (s, C5a), 142.3 (s, C10a), 143.9 (s, C9), 145.1 (d, C7), 158.4 (s, C4). HRMS m/z calculated for C$_{18}$H$_{16}$N$_4$O$_5$S: 368.0943; found: 368.0941.

Example 41

4-Chloro-9-tosylaminopyrido[3',2':4,5]pyrrolo[1,2-c]pyrimidine (23c)

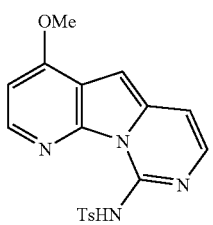

Following the methodology for 23a., from 4-chloro-9-tosylamino-6-hydroxypyndo[3',2':4,5]pyrrolo[1,2-c]pyrimidine (165 mg, 0.42 mmol) compound 23c (104 mg, 66%) was obtained.

IR (KBr) ν3265 (m, NH), 1602 (s, C=N), 1396, 1281 (m, SO$_2$), 1141. $^1$H-NMR (DMSO-d$^6$, 300 MHz) δ 2.4 (s, 3H, Me), 6.80 (s, 1H, H5), 6.84 (d, J 7.8, 1H, H6), 7.17 (d, J 7.8, 1H, H7), 7.37 (d, J 7.8, 2H1, Ts), 7.58 (d, J 4.8, 1H, H3), 8.03 (d, J 7.8, 2H, Ts), 8.45 (d, J 4.8, 1H, H2), 11.20 (br, 1H, NH). $^{13}$C-NMR (DMSO-d$^6$, 50 MHz) δ 21.0 (q, Me), 93.7 (d, C5), 101.3 (d, C6), 119.9 (d, C3), 122.5 (s, C4a), 125.9 (d, Ts), 126.3 (d, C2), 129.4 (d, Ts), 133.5 (s, C5a), 135.6 (s, Ts), 142.5 (s, C10a), 143.5 (d, C7), 143.8 (s, C9), 145.3 (s, C4). MS (EI) m/z 374 ($^{37}$ClM$^+$, 5), 372 ($^{35}$ClM$^+$, 12), 309 ($^{37}$ClM-SO$_2$, 24), 307 ($^5$ClM-SO$_2$, 63). HRMS m/z calculated for C$_{17}$H$_{13}$ClN$_4$O$_2$S: 372.0448; found: 372.0444.

Example 43

5-Iodo-9-tosylaminopyrido[3',2':4,5]pyrrolo[1,2-c]pyrimidine (24a)

To a solution of 23a (10 mg, 0.03 mmol) in CH$_2$Cl$_2$ (5 ml) at −30° C. N-iodosuccinimide (7 mg mg, 0.03 mmol) was portionwise added and the mixture was stirred for 15 min. The solution was washed with water and the organic solutions was dried, filtered and evaporated to obtain 24a (14 mg, 95%) as a yellow solid.

IR (KBr) ν3264 (m, NH), 1599 (m, N=C), 1393 (m, C—N), 1140. $^1$H-NMR (CD$_3$OD, 300 MHz) δ 2.37 (s, 3H, Me), 6.61 (d, J 7.5, 1H, H6), 7.15 (d, J7.5, 1H, H7), 7.34 (d, J 8.4, 2H, Ts), 7.46 (dd, J 7.5 and 4.8, 1H, H3), 7.81 (dd, J 7.5 and 1.5, 1H, H4), 8.07 (d, J 8.4, 2H, Ts), 8.46 (dd, J 4.8 and 1.5, 1H, H2). MS (EI) m/z 464 (M$^+$, 13), 399 (M-SO$_2$, 32), 338 (M-I, 1), 309 (M-Ts, 5), 273 (M-SO$_2$-I, 33), 182 (M-Ts-I, 58). HRMS m/z calculated for C$_{17}$H$_{13}$IN$_4$O$_2$S: 463.9804; found: 493.9799.

Example 44

5Iodo-4-methoxy-9-tosylaminopyrido[3',2':4,5]pyrrolo[1,2-c]pyrimidine (24b)

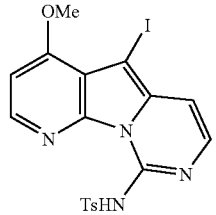

Following the methodology for 24a, from 23b (250 mg, 0.68 mmol) compound 24b (295 mg, 95%) was obtained as a light yellow solid.

IR (KBr) ν3259 (m, NH), 1592 (s, C=N), 1293 (m, SO$_2$), 1142. $^1$H-NMR (DMSO-d$^6$, 200 MHz) δ 2.33 (s, 3H, Me), 3.97 (s, 3H, Me), 6.62 (d, J 7.7, 1H, H6), 7.06 (d, J 5.6, 1H, H3), 7.18 (d, J 7.7, 1H, H7), 7.35 (d, J 8.2, 2H, Ts), 8.02 (d, J 8.2, 2H,Ts), 8.40(d,J 5.6, 1H, H2), 11.15 (br, 1H, NH). $^{13}$C-NMR (DMSO-d$^6$, 50 MHz) δ 21.0 (q, Me), 56.2 (q, Me), 102.1 (d, C3), 113.9 (s, C4a), 126.1 (d, Ts), 129.4 (d, C2 and Ts), 133.9 (s, C5a), 142.6 (s, C10a), 143.4 (s, C9), 145.1 (d, C7), 159.0 (s, C4). MS (EI) m/z 494 (M$^+$, 31), 429 (M-SO$_2$, 65), 368 (M-I, 12), 339 (M-Ts, 15), 303 (M-SO$_2$-I, 58), 212 (M-Ts-I, 100). HRMS m/z calculated for C$_{18}$H$_{15}$IN$_4$O$_5$S: 493.9909; found: 493.9891.

Example 45

4-Methoxy-9-tosylamino-5(2-acetylaminopyrimidin-4-yl) pyrido[3',2':4,5]pyrrolo[1,2-c]pyrimidine (25)

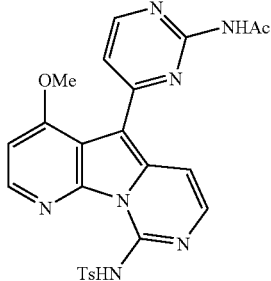

A solution of 24b (295 mg, 0.60 mmol), 27 (258 mg, 0.9 mmol), $Pd_2(dba)_3 \cdot CHCl_3$ (120 mg, 0.12 mmol), $PPh_3$ (60 mg, 0.24 mmol), LiCl (74 mg, 1.8 mmol) and CuI (23 mg, 0.12 mmol) in dioxane (25 mL) was refluxed for one hour. The solvent was evaporated and the crude dissolved in $CH_2Cl_2$. The organic solution was extracted three times with 4N HCl solution. The aqueous solutions were basified together with solid $NaHCO_3$ and extracted with $CH_2Cl_2$. The organic solution was evaporated and the mixture was purified by flash column chromatography. Elution with $CH_2Cl_2$/MeOH (99/1) gave 23b (66 mg, 28%) and with $CH_2Cl_2$/MeOH (9/1) gave 25 (209 mg, 71%) as a yellow solid.

IR (KBr) v3379 (m, NH), 1592 (s, C=N), 1474, 1449, 1422, 1293 ($SO_2$), 1143. $^1$H-NMR ($CDCl_3$, 200 MHz) δ 2.41 (s, 3H, Me), 2.47 (s, 3H, Me), 4.05 (s, 3H, Me), 6.92 (br, 1H, H3), 7.31 (d, J 8.4, 2H, Ts), 7.46 (brd, 1H, H6), 7.60 (d, J 6.6, 1H, H7), 7.98 (br, 1H, H5'), 8.12 (d, J 8.4, 2H, Ts), 8.38 (br, 1H, H2), 8.50 (br, 1H, H6'). MS (ES+) m/z 505 (M+2, 30), 504 (M+1, 100).

Example 46

4Hydroxy-9-tosylamino-5-(2-aminopyrimidin-4-yl) pyrido[3',2':4,5]pyrrolo[1,2-c]pyrimidine (26)

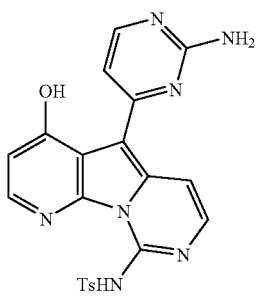

A solution of 25 (10 mg, 0.02 mmol) in HBr (48%) was refluxed for 10 min. The solution was basified with $NaHCO_3$ and extracted with $CH_2Cl_2$. The organic solution was dried, filtrated and evaporated to obtain 26 (7 mg, 78%) as a yellow solid.

$^1$H-NMR ($CDCl_3$+$CD_3OD$, 300 MHz) δ 2.34 (s, 3H, Me), 6.76 (d, J 6.6, 1H, H6), 7.03 (d, J 6.6, 1H, H5'), 7.06 (d, J 6.6, 1H, H5'), 7.23 (d, J 8.1, 2H, Ts), 7.65 (d, J 6.6, 1H, H7), 8.00 (d, J 8.1, 2H, Ts), 8.01 (d, J 6.6, 1H, H6'), 8.23 (brd, 1H, H2). MS (ES+) m/z 449 (M+1, 10), 448 (M+, 100).

Example 47

4-Chloro-2-methanesulfonylpyrimidine

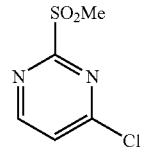

See *Heterocycles*, 1977, 8, 299. To a solution of 4-chloro-2-methanesufenylpyrimidine (5 g, 31 mmol) in $CH_2Cl_2$ (100 ml) mCPBA (16.12 g, 94 mmol) was added and stirred for 2 h. at room temperature. The mixture was washed with saturated aq. $Na_2S_2O_3$ and the aqueous solution basified with saturated aq. $Na_2CO_3$. The organic layer was separated and the aqueous solution extracted with $CH_2Cl_2$. The organic layers were evaporated together to obtain 4chloro-2-methanesulfonylpyrimidine (5.5 g, 92%) as a white solid.

$^1$H-NMR ($CDCl_3$, 200 MHz) δ 3.39 (s, 3H, Me), 7.61 (d, J 5.4, 1H, H5), 8.83 (d, J 5.4, 1H, H6). MS (CI, CH) m/z 192 ($M^{35}Cl^+$, 1), 157 (M-Cl, 1), 97 (100).

Example 48

2-Amino-4-chloropyrimidine

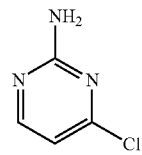

To a solution of 4-chloro-2-methanesulfonylpyrimidine (5 g, 26 mmol) in i-PrOH (20 ml) 20% aq. $NH_3$ (20 ml) was added and the mixture stirred for 20 min. at room temperature. The mixture was extracted with $CH_2Cl_2$ four times and the organic solvent removed under vacuum. 2-Amino-4-chloropyrimidine (3.3 g, 100%) was obtained as a white solid.

$^1$H-NMR ($CDCl_3$, 200 MHz) δ 5.26 (br, 2H, $NH_2$), 6.67 (d, J 5.2, 1H, H5), 8.17 (d, J 5.2, 1H, H6). MS (CI, $CH_4$) m/z 132 ($^{37}$ClM+1, 33),131 ($^{37}$ClM$^+$, 2), 130 ($^{35}$ClM+1, 87), 129 ($^{35}$ClM, 8), 97 (100), 94 (M-Cl, 53).

Example 49

2-Acetylamino-4-chloropyrimidine and 4-Chloro-2-diacetylaminopyrimidine

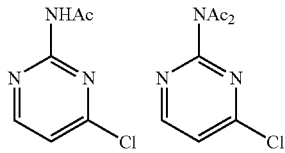

A solution of 2-amino-4-chloropyrinmidine (500 mg, 3.9 mmol) in acetic anhydride (20 ml) was refluxed for 30 min. The solvent was removed under vacuum and the remaining oil was dissolved in saturated aq. $Na_2CO_3$. The aqueous solution was extracted with $CH_2Cl_2$. The organic solution was dried and evaporated to give an oil which was purified by flash column chromatography. Elution with $CH_2Cl_2$/hexane (2/1) gave 4-Chloro-2-diacetylaminopyrimidine (122 mg, 16%) as a white solid and with $CH_2Cl_2$ yielded 2-Acetylamino-4-chloropyrimidine (270 mg, 45%) as a white solid.

2-Acetylamino-4-chloropyrimidine

¹H-NMR (CDCl₃, 200 MHz) δ 2.51 (s, 3H, Me), 7.04 (d, J 5.3, 1H, H5), 8.17 (d, J 5.3, 1H, H6). ¹³C-NMR (CDCl₃, 50 MHz) 625.3 (q, Me), 116.0 (d, C5), 157.5 (s, C4), 159.2 (d, C6), 161.8 (s, C2). MS (EI) m/z 173 (³⁷ClM, 5), 171 (³⁵ClM, 16), 131 (³⁷ClM-Ac, 32), 129 (³⁵ClM-Ac, 100).

4-Chloro-2-diacetylaminopyrimidine

¹H-NMR (CDCl₃, 200 MHz) δ 3.32 (s, 6H, 2Me), 7.45 (d, J 5.2, 1H, H5), 8.76 (d, J 5.2, 1H, H6). ¹³C-NMR (CDCl₃, 50 MHz) δ 26.3 (q, Me), 121.2 (d, C5), 160.0 (d, C6), 163.1 (s, C4), 171.6 (s, C2). MS (CI, CH₄) m/z 215 (³⁷ClM, 1), 214 (³⁷ClM-1, 3), 213 (³⁵ClM, 1), 212 (³⁵ClM-1, 5), 174 (³⁷ClM-Ac, 32), 172(³⁵ClM-Ac, 100).

Example 50

2-Acetylamino-4-trimethylstannylpyrimidine (27)

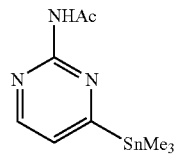

A solution of 2-Acetylamino-4-Chloropyrimidine (170 mg, 1.0 mmol), hexamethylditin (400 μl, 1.8 mmol) and Pd(PPh₃)₄ (40 mg, 0.03 mmol) in dioxane (6 ml), was refluxed for 1 h. The solvent was removed under vacuum and the residue purified by neutral alumina column chromatography. Elution with hexane/AcOEt (7/3) gave 27 (240 mg, 80%) as a white solid.

¹H-NMR (CDCl₃, 300 MHz) δ 0.36 (s, 9H, 3Me), 2.53 (s, 3H, Me), 7.13 (d, J 4.8, 1H, H5), 7.98 (br, 1H, NH), 8.35 (d, J 4.8, 1H, H6). ¹³C-NMR (CDCl₃, 75 MHz) δ-9.5 (q, 3Me), 25.3 (q, Me), 124.4 (d, C5), 154.7 (d, C6). MS (EI) m/z 300 (¹²⁰SnM⁺, 1), 285 (¹²⁰SnM-Me, 34) 270 (¹²⁰SnM-2 Me, 1), 255 (¹²⁰SnM-3Me, 6), 244 (¹²⁰SnM-3Me-Ac, 30), 136 (M-SnMe₃, 100).

What is claimed is:

1. A compound of the formula (I):

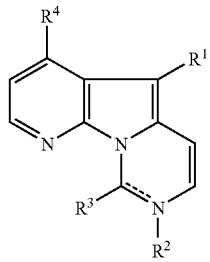

wherein:
R¹ is an optionally substituted pyrimidinyl group;
R² is hydrogen when the dotted line is absent, or R² is absent when the dotted line represents a bond to give a double bond between the nitrogen which bears R² and the carbon which bears R³;
R³ is an oxo group ═O when the dotted line is absent, or is an amino group or a substituted amino group when the dotted line represents a bond to give a double bond between the nitrogen bearing R² and the carbon bearing R³;
R⁴ is hydrogen;
or a pharmaceutically acceptable salt thereof.

2. A compound according to claim 1, wherein R¹ is an unsubstituted 4-pyrimidyl group.

3. A compound according to claim 1, wherein the 4-pyrimidyl group is substituted.

4. A compound according to claim 1, wherein R² is hydrogen.

5. A compound according to claim 1, wherein R³ is an oxo group.

6. A compound according to claim 1, wherein the dotted line represents a bond.

7. A compound according to claim 1, wherein:
R¹ is a 4-pyrimidyl group substituted at the 2-position with amino, N-acylamino, or methylthio;
R² is absent; and
R³ is an amino group or a protected amino group, or N-acyl.

8. A compound according to claim 1, wherein the compound is:
8,9-dihydro-5-(2-methanesulfanylpyrimidin-4-yl)pyrido[3',2':4,5]pyrrolo[1,2-c]-pyrimidin-9-one of formula:

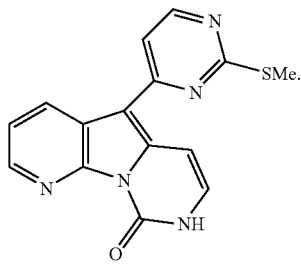

9. A compound according to claim 1, wherein the compound is 9-amino-5-(2-methanesulfanylpyrimidin-4-yl)pyrido[3',2':4,5]pyrrolo[1,2-c]pyrimidine of formula:

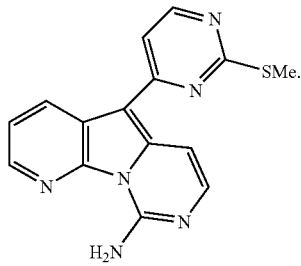

10. A compound according to claim 1, wherein the compound is 9-acetylamino-5-(2-methanesulfanylpyrimidin-4-yl)pyrido[3',2':4,5]-pyrrolo-[1,2-c]pyrimidine of formula:

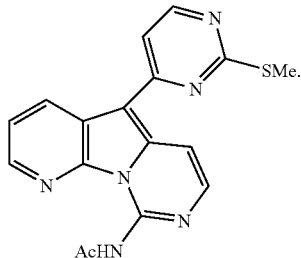

11. A compound according to claim 1, wherein the compound is 9-amino-5-(2-methanesulfinylpyrimidin-4-yl)pyrido[3',2':4,5]pyrrolo[1,2-c]pyrimidine of formula:

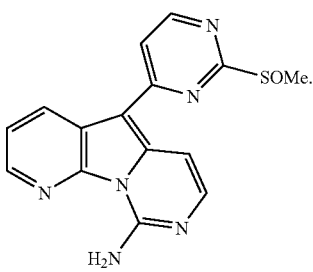

12. A compound according to claim 1, wherein the compound is 9-amino-5-(2-methanesulfonylpyrimidin-4-yl)pyrido[3',2':4,5]pyrrolo[1,2-c]pyrimidine of formula:

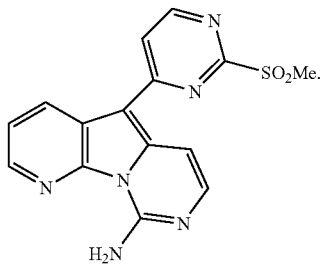

13. A compound according to claim 1, wherein the compound is 9-amino-5-(2-aminopyrimidin-4-yl)pyrido[3',2':4,5]pyrrolo[1,2-c]-pyrimidine of formula

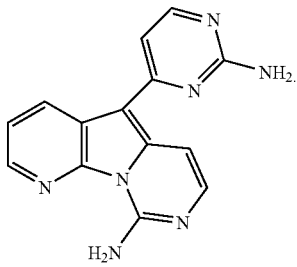

14. A method for preparing a compound according to claim 1, the method comprising reacting an optionally substituted 5-halopyrido(3',2':4,5)pyrrolo(1,2-c)pyrimidine or 8,9-dihydro-5-halopyrido(3',2':4,5)-pyrrolo(12-c)pyrimid-9-one with a trimethyistannylpyrimidine compound.

15. The method of claim 14, wherein the method further comprises modifying and/or replacing one or more substituents present on the compound that is obtained after reacting the optionally substituted 5-halopyrido(3',2':4,5)pyrrolo 1,2-c)pyrimidine or 8,9-dihydro-5-halopyrido(3',2':4,5)-pyrrolo (1,2-c)pyrimid-9-one with the trimethylstannylpyrimidine compound.

16. An intermediate compound which is an optionally substituted 5-halopyrido[3',2':4,5]pyrrolo[1,2-c]pyrimidine or 8,9-dihydro-5-halopyrido[3',2':4,5]-pyrrolo[1,2-c]pyrimid-9-one of formula:

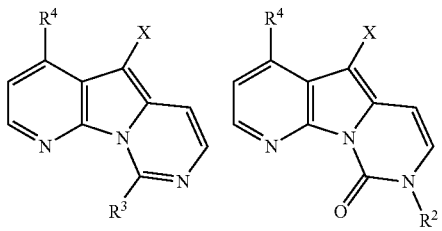

X is halo;

$R^2$ is hydrogen or a nitrogen protecting group;

$R^3$ is an amino group or a protected amino group; and $R^4$ is hydrogen.

17. An intermediate compound according to claim 16, wherein X is iodo, $R^2$ is a protecting group, and $R^3$ is a protected amino group.

18. A pharmaceutical composition comprising a compound according to claim 1 with a pharmaceutically acceptable carrier.

19. A pharmaceutical formulation for combination therapy, comprising a compound according to claim 1, and at least one other therapeutically active compound.

20. A method for the treatment of leukemia, lung cancer, or colon cancer, the method comprising administering to a subject in need of such treatment an effective amount of a compound of claim 1 or a pharmaceutically acceptable salt thereof.

21. The method of claim 20, wherein the cancer is leukemia.

22. The method of claim 20, wherein the cancer is lung cancer.

23. The method of claim 20, wherein the cancer is colon cancer.

* * * * *